(12) United States Patent
Gao

(10) Patent No.: US 7,002,042 B2
(45) Date of Patent: Feb. 21, 2006

(54) CATIONIC LIPOSOMES FOR GENE TRANSFER

(75) Inventor: Xiang Gao, Nashville, TN (US)

(73) Assignee: Vanderbilt University, Nashville, TN (US)

(*) Notice: Subject to any disclaimer, the term of this patent is extended or adjusted under 35 U.S.C. 154(b) by 228 days.

(21) Appl. No.: 10/224,706

(22) Filed: Aug. 20, 2002

(65) Prior Publication Data

US 2003/0049310 A1 Mar. 13, 2003

Related U.S. Application Data

(62) Division of application No. 09/447,688, filed on Nov. 23, 1999, now Pat. No. 6,656,498.
(60) Provisional application No. 60/109,950, filed on Nov. 25, 1998, and provisional application No. 60/110,970, filed on Dec. 4, 1998.

(51) Int. Cl.
C07C 233/05 (2006.01)
C07C 237/06 (2006.01)
C07C 237/16 (2006.01)
C07C 211/18 (2006.01)
C07C 211/08 (2006.01)

(52) U.S. Cl. .................. 564/153; 564/159; 564/291; 564/295; 564/509; 564/511; 564/512
(58) Field of Classification Search ................ 564/153, 564/159, 291, 295, 509, 511, 512
See application file for complete search history.

(56) References Cited

U.S. PATENT DOCUMENTS

| | | | |
|---|---|---|---|
| 4,386,026 A | 5/1983 | Ponpipom et al. | |
| 5,366,737 A | 11/1994 | Eppstein et al. | |
| 5,446,023 A | 8/1995 | Pavia et al. | |
| 5,459,127 A | 10/1995 | Flegner et al. | |
| 5,580,859 A | 12/1996 | Flegner et al. | |
| 5,589,466 A | 12/1996 | Flegner et al. | |
| 5,635,487 A | 6/1997 | Wolff et al. | |
| 5,703,055 A | 12/1997 | Flegner et al. | |
| 5,759,519 A | 6/1998 | Sridhar et al. | |
| 6,348,499 B1 | 2/2002 | Felgner et al. | |
| 6,433,017 B1 | 8/2002 | Felgner et al. | |

FOREIGN PATENT DOCUMENTS

| DE | 4229016 | 3/1994 |
|---|---|---|
| WO | WO 00/31022 | 6/2000 |

OTHER PUBLICATIONS

Database CAPLUS on STN, Acc. No. 1984:104109, Cohen et al., DE 3320720 (Dec. 8, 1983) (abstract).*
Database CAPLUS on STN, Acc. No. 1967:29611, Pierce FR 1443909 (Jul. 1, 1966) (abstract).*
Database CAPLUS on STN, Acc. No. 1985:456596, Yushiro Chem. Industry Co., Ltd., JP 60049094 (Mar. 18, 1985) (abstract).*
Database CAPLUS on STN, Acc. No. 1985:9498, Maddonado et al., FR 2539754 (Jul. 27, 1984) (abstract).*
Advertisement for GenePort Transfection Reagent published no earlier than Nov. 27, 1998.
Marketing material for GenePorter™ Transfection Reagent publicly available no earlier than Nov. 27, 1998.
Berge et al., "Pharmaceutical Salts," *J. Pharmac. Sci.* 66(1):1–19 (1977).
Brigham et al. "Expression of Human Growth Hormone Fusion Genes in Cultured Lung Endothelial Cells and in the Lungs of Mice," *Am. J. Respir. Cell Mol. Biol.* 8:209–213 (1993).
Brigham et al., "Cationic Lipid–Based Gene Delivery: An Update," Gene Therapy for Diseases of the Lung, "Lung Biology in Health and Disease Series," edited by C. Lenfant, 104:99–112 (1997).
Brigham et al., "Rapid Communication: In vivo Transfection of Murine Lungs with a Functioning Prokaryotic Gene Using a Liposome Vehicle," *Am. J. Med. Sci.* 298(1):278–281 (1989).
Cech et al., "Biological Catalysis By RNA," *Ann. Rev. Biochem.* 55:599–629 (1986).
Düzgünes, "Membrane Fusion," *Subcellular Biochemistry*, Donald B. Roodyn, ed., Plenum Press, New York 11(5):195–287.
Felgner et al., "Enhanced Gene Delivery and Mechanism Studies with a Series of Cationic Lipid Formulations," *J. Biol. Chem.*, 28:2550–2561.
Felgner et al., "Lipofection: A highly efficient, lipid–mediated DNA–transfection procedure," *Proc. Natl. Acad. Sci.* 84(21):7413–7417 (1987).
Gao et al., "Cationic Lipsome–Mediated Gene Transfer," *Gene Therapy* 2:710–722 (1995).
Gillies et al., "Expression On Human Anti–Tetanus Toxoid Antibody In Transfected Murine Myeloma Cells," *Bio/Tech.* 7:799–804 (1989).
Goodfellow, "Steady steps lead to the gene," *Nature* 341:102–103 (1989).
Hampel et al., "Hairpin' catalytic RNA model: evidence for helices and sequence requirement foe substrate RNA," *Nucl. Acids Res.* 18(2):299–304 (1990).
Haseltine et al., "The Molecular Biology of the AIDS Virus," *Sci. Am.* 52–62 (1988).

(Continued)

Primary Examiner—Brian Davis
(74) Attorney, Agent, or Firm—Needle & Rosenberg, P.C.

(57) ABSTRACT

The present invention relates to synthetic cationic lipids, liposome formulations and the use of such compounds to introduce functional bioactive agents into cultured cells.

1 Claim, 6 Drawing Sheets

OTHER PUBLICATIONS

Hong et al., "Stabilization of cationic liposome–plasmid DNS complexes by polyamines and poly(ethylene glycol)–phospholipid conjugates for efficient in vivo gene delivery," FEBS Letters 400(2):233–237 (1997).

Kunkel et al., "Duchenne/Becker muscular dystrophy: a short overview of the gene, the protein, and current diagnostics," Bri. Med. Bull. 45(3):630–643 (1989) (abstract).

Lee et al., "Detailed Analysis of Structure and Formulations of Cationic Lipids for Efficient Gene Transfer to the Lung," Human Gene Ther. 7:1701–1717 (1996).

Lerouge et al., "Isolation and Structural Characterization of a New Non–Phosorylated Lipoamine Acid from Mycobacterium Phlei," (abstract) Chem. Phys. Lipids, Database CAPLUS on CAS, 110: 131850 (1988).

Leventis et al., "Interactions of Mammalian Cells with Lipid Dispersions Containing Novel Metabolizable Cationic Amphphiles," Biochem. Biophys Acta. 1023:124–132 (1993).

Li et al., "In vivo gene transfer via intravenous administration of cationic lipid–protamine–DNA (LPD) complexes," Gene Therapy 4:891–900 (1997).

Litzinger et al., "Fate of Cationic Liposomes and Their Complex with Oligonucleotide in vivo," Biochem. Biophys. Acta. 129(2):139–149 (1996).

Liu et al., "Factors controlling the efficiency of cationic lipid–mediated transfection in vivo via intravenous administration," Gene Therapy 4(6)517–523 (1997) (abstract).

Liu et al., "Factors influencing the efficiency of cationic liposome–mediated intravenous gene delivery," Nat. Biotech. 15(2):167:173 (1997).

Matsukura et al., "Regulation of viral expression of human immunodeficiency virus in vitro by an antisense phosphorothioate oligodeoxynucleotide against rev (art/trs) in chronically infected cells," Proc. Natl. Acad. Sci. 86(11):4244–4248 (1989).

McLean et al., "Organ Specific Endothelial Cell Uptake of Cationic Liposome–DNA Complexes in Mice," Am. J. Physiol. 273(1Pt2):H387–H404 (1997).

Senior et al., "Interaction of Positively–Charged Liposomes with Blood: Implications for their Application in vivo," Biochimica et Biophysica Acta 1070:173–179 (1991).

Solodin et al., "A Novel Series of Amphiphillic Imidazolinium Compounds for in Vitro and in Vivo Gene Delivery," Biochemistry 34(41):13537–13544 (1995).

Templeton et al., "Improved DNA: Liposome complexes for increased systemic delivery and gene expression," Nat. Biotech. 15(7):647–652 (1997).

Thierry et al., "Systemic Gene Therapy: Biodistribution and Long–Term Expression of a Transgene in Mice," Proc. Natl. Acad. Sci. 92:9742–9746 (1995).

Ward et al., "Binding activities of a repertoire of single immunoglobin variable domains secreted from Escherichia coli," Nature 341:544–546 (1989).

Zelphati et al., Effect of Serum Components on the Physico–Chemical Properties of Cationic Lipid/Oligonucletide Complexes and on Their Interactions with Cells, Biochim. Biophys. Acta 1390:119–133 (1998).

* cited by examiner

| # | CATATONIC LIPIDS | STRUCTURE |
|---|---|---|
| 8 | MPET | 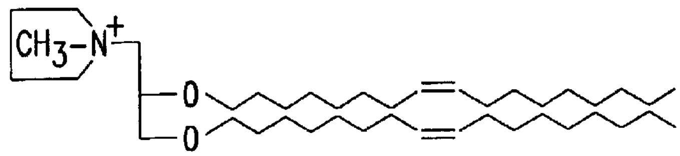 |
| 9 | MPES | 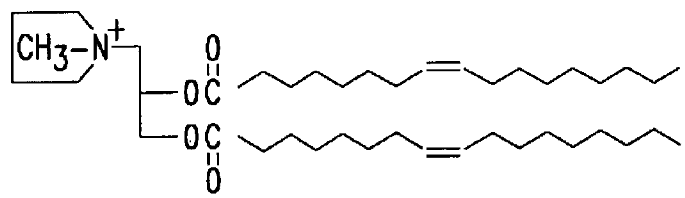 |
| 10 | DODHEM | 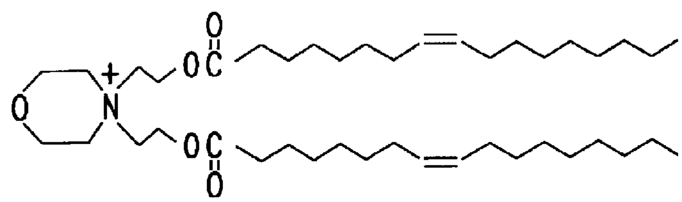 |
| 11 | MMPSDOG | 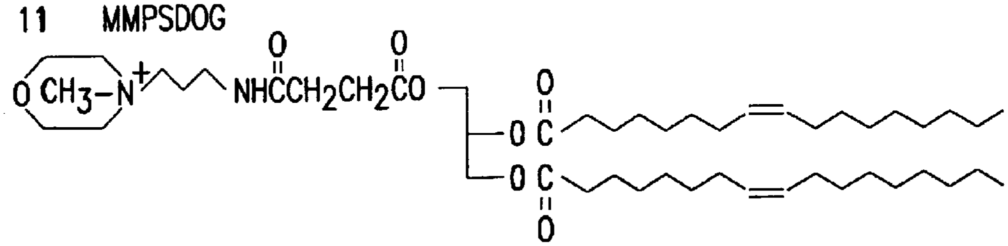 |
| 12 | DOBDMA | 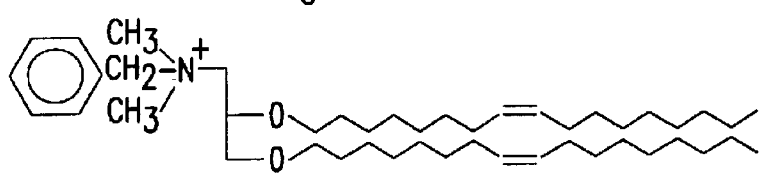 |
| 13 | DOBDMAP | 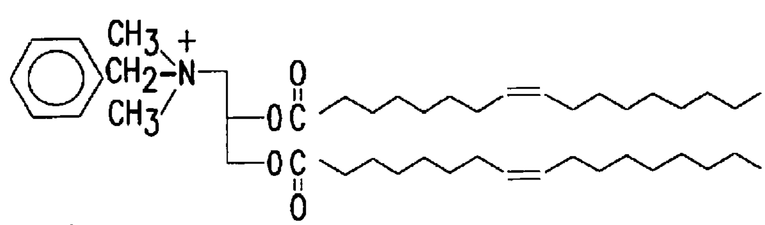 |

CATIONIC LIPOSOMES FOR GENE TRANSFER

CROSS REFERENCE TO RELATED APPLICATIONS

This application is a divisional of and claims the benefit of, U.S. application Ser. No. 09/447,688, filed Nov. 23, 1999, now U.S. Pat. No. 6,656,498. U.S. application Ser. No. 09/447,688 claims the benefit of U.S. Provisional Application Nos. 60/109,950, filed Nov. 25, 1998 and 60/110,970, filed Dec. 4, 1998. U.S. Application Nos. 09/447,688, 60/109,950, and 60/110,970 are each incorporated herein by this reference in their entireties.

STATEMENT OF GOVERNMENT INTEREST

This invention was made with government support under Grant Nos. NIH 5 P50 HL 19153, NIH 5 RO1 HL 45151 and NIH 5 RO1 AI 31900 awarded by the National Institutes of Health to Vanderbilt University. The U.S. Government has certain rights in the invention.

FIELD OF THE INVENTION

This invention relates to synthetic cationic lipid compounds, liposome formulations and the use of such compounds via lipofection to introduce functional bioactive agents/biologically active substances to cultured cells.

BACKGROUND OF THE INVENTION

Lipofection (or transfection), a process of introducing functional nucleic acids into cultured cells by using positively charged liposomes, was first described by Philip Felgner et al. a decade ago, and later shown, by K. L. Brigham, as applicable in vivo to experimental animals. See, Felgner et al., *Proc. Natl. Acad. Sci. USA*, 84, 74113–7417 (1987) and K. L. Brigham et al., *Am. J. Med. Sci.*, 298, 278–281 (1989). Cationic lipids have become an increasingly important tool for many in vitro gene transfer applications, including several recent human gene therapy trials. As non-viral, synthetic DNA carriers, cationic lipids are particularly attractive because they are non-immunogenic, simple to use, can deliver DNA of a broad range size, and can be manufactured in large quantity. Although lipofection is quite efficient in vitro under serum-free conditions, its use in vivo when delivered as DNA/lipid complex, lipoples, via intravenous or airway routes, was limited to the presence of proteins and polysaccharides in the body fluids and mucus that strongly inhibit the transfection efficiency. Recent efforts to search for more efficient lipids and/or improved DNA/liposome formulations have resulted in dramatic increases of in vivo transfection efficiency. See, Solodin, I. et al., *Biochemistry*, 34, 13537–13544 (1995); Templeton, N. S., et al., *Nat. Biotech.*, 15(7), 647–652 (1997); Thierry, A. R. et al., *Proc. Natl. Acad. Sci. USA*, 92, 9742–9746 (1995); Li, S. et al., *Gene Ther.*, 4, 891–900 (1997); Liu, Y., et al., *Nat. Biotechnol.*, 15(2), 167–173 (1997); Liu, F. et al., *Gene Ther.*, 4(6), 517–523 (1997); and Song Y. K., et al., *Hum. Gene Ther.*, 8, 1585–1594 (1997).

Using a few well known cationic lipids, researchers have carefully studied key parameters that affect transfection efficiency of intravenously administered lipoplex in mouse. See, also Hong K., et al., *FEBS Letters*, 400, 233–237 (1997). These studies have shown that a 2–16 fold excess of cationic liposome over DNA were necessary for high level gene expression in lungs and other organs, liposomes composed of 1,2,-dioleyl-3-N,N,N-trimethyl amino propane chloride (DOTMA) were significantly more active than that composed other cationic lipids. See, Song et al. Liposomes prepared from pure cationic lipid, such as DOTMA or 1,2-dioleoyl-3-trimethylammonium propane (DOTAP), or mixtures of a cationic lipid and cholesterol or Tween 80 could mediate more efficient gene transfer than those formulations composed of a cationic lipid and a neutral phospholipid 1,2-dioleoyl-sn-glycero-3-phosphotidylethanolamine (DOPE) and the lipoplex prepared from extruded multilamellar liposomes were more active than those prepared from sonicated small unilamellar liposomes. See, Hong et al., Liu, Y et al., Liu, F. et al, Song et al., and Li, S. et al. With these improvements, the level of reporter gene expression in lungs after intravenous administration of optimized lipoplex were estimated 100 to 1000 fold more efficient than those prepared according to previously reported studies using DOTMA/DOPE liposomes and less lipid to DNA ratios. However, the improvements were also associated with noticeable toxicity of varying degrees of lipid/DNA treated animals due to toxic effect of large excess of cationic lipids or lipoplexes themselves. Therefore, searching for cationic lipids with less toxicity and formulations that function at reduced lipid to DNA ratios seem to be reasonable approaches to the problem of lipofection-related toxicity. We report the synthesis of a novel series of cationic lipids and test of their in vivo transfection activity in mice.

High level transfection in vivo in lungs and several other organs using lipoplex have been reported by a number of groups, as cited in the text above. One of the conclusions drawn from these studies is that relatively high lipid to DNA ratios is required to achieve high levels of transfection in vivo (Hong, K., et al., Liu, Y., et al., Liu, F., et al., and Li, S., et al.) Besides the high charge ratios, other factors such as the use of cholesterol, instead of DOPE as helper lipid (Hong, K., et al., Templeton, N. S., et al., Liu, Y., et al, Song, Y. K., et al. and Li, S., et al); multilamellar liposomes of about 200 nm in size rather than small unilamellar liposomes (Liu, Y., et al.) and the use of polycations and polymers in the cationic lipid-DNA complexes also contribute to the high level transfection (Hong, K., et al. and Li, S., et al.). The least mentioned factor in these studies was the side effects that are associated with these high level transfections in vivo.

It is therefore an object of the present invention to provide cationic lipids which are less toxic in pharmaceutical formulations and function at reduced lipid to DNA ratios than existing cationic lipids.

It is also an object of the present invention to provide a liposome, with or without a helper lipid, which is less toxic than prior art liposomes.

It is also an object of the present invention to provide cationic liposome pharmaceutical formulations which enhance intracellular delivery of DNA to a less toxic extent than previously described lipophilic compounds.

It is also an object of this invention to provide a lipoplex that has a transfection activity which is higher than transfection activity of the prior art liposome.

It is also and object of this invention to provide improved lipid and liposome formulation for treating a disease in a mammal via transfection.

It is a further object of the present invention to provide cationic liposome formulations which demonstrate superior efficacy.

SUMMARY OF THE INVENTION

In accordance with the purpose(s) of this invention, as embodied and described herein, this invention, in one aspect, relates to novel cationic lipids, and their use in pharmaceutical formulations for the intra cellularly delivery of bioactive agent.

One aspect of the invention relates to a compound of the general formula I:

(I)

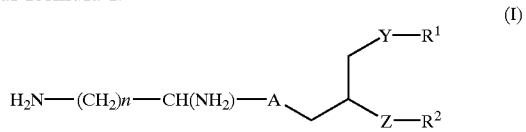

or a pharmaceutically acceptable salt or ester thereof; wherein:
$R^1$ and $R^2$ are the same or different and are from $C_6$ to $C_{24}$ alkyl or aryl;
Y and Z are both —O—C(O)— or —O—;

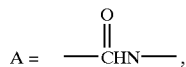

or —C(O)—O—; and
n=1–6.

Another aspect of the invention relates to a compound of formula I(a):

(Ia)

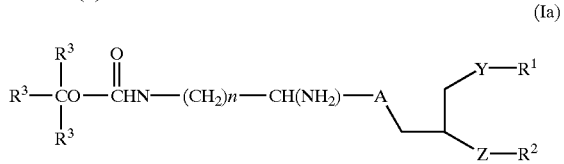

or a pharmaceutically acceptable salt or ester thereof, wherein:
$R^1$ and $R^2$ are independently from $C_6$ to $C_{24}$ alkyl or alkenyl or one of $R^1$ or $R^2$ is $C_6$ to $C_{24}$ alkyl or alkenyl and the other is absent, or $R^1$ and $R^2$ are independently aryl;
Y and Z are the same and are —O—C(O)—, or one of Y and Z is —O—C(O)— and the other is —OH;

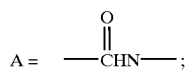

$R^3$ is $C_{1-6}$ alkyl, aryl, aryloxy, alkene, or a protecting group; and
n=1–6.

Another aspect of the invention relates to a compound of formula I(b):

(Ib)

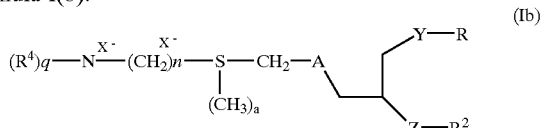

or a pharmaceutically aceptable salt or ester thereof, wherein:
$R^1$ and $R^2$ are the same or different and are from $C_6$ to $C_{24}$ alkyl or alkenyl or aryl;
Y and Z are both —O—C(O)—;
A is —C(O)—O—;
$R^4$ is $C_{1-6}$ alkyl;
a=0 or 1;
n=1–3;
q=0–3;
$X^-$ is a halogen anion or is absent; and
the S and N atoms each independently have a positive charge or the positive charge is absent.

The novel N-[(2,3-dioleoyloxy)propyl]-L-lysinamide (LADOP) cationic lipid has lysine as a head group and two long fatty chains as lipid anchors linked through biodegradable diester and amide bonds. Liposome/DNA complexes prepared with a plasmid containing a luciferase reporter gene delivered either intravenously or intratracheally to mice demonstrated high level expression of the transgene. The magnitude of transgene expression was related to the ratio of lipid to DNA; high level of transgene expression occurred when lipid/DNA charge ratios reached 1:8 to 1:24. The duration of the transgene expression in lungs of mice treated with liposome/DNA complex delivered intravenously was transient, disappearing by 48 hours after transfection. However, a second intravenous transfection at 48 hours after the first injection resulted in almost identical gene expression and duration.

The LADOP cationic lipid is a very efficient molecule as a result of careful design. The overall structure offers a bilayer-forming lipid with good membrane fluidity. Therefore, the novel lipid can actively transfer genes without a commonly required helper lipid, DOPE. LADOP has a stable amide bond linkage between the head group and the lipid anchor to ensure stability in solution. It has two cationic charges, while lysl-PE has only one net charge per molecule. The diester bonds in LADOP render the lipid biodegradable. This feature has been demonstrated in our in vivo studies in which the animals tolerated repeated intravenous doses of DNA/LADOP complex well and transgene expression patterns of the first injection and second injection shortly after were identical both in magnitude and duration. In two recent reports, a twenty day interval between treatments was needed for effective repeat administration, using DOTMA and DOTAP, two formulations that have been widely used. The fact that the novel LADOP cationic compound mediated efficient transfection both intravenously and intratracheally, together with features such as simplicity of synthesis and formulation and minimal toxicity, make this a very attractive and useful reagent for in vivo gene delivery, and ultimately, gene therapy.

Another aspect of the invention relates to lysine amide cationic compounds of the general formula III:

(III)

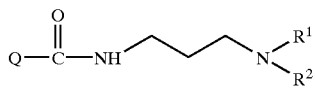

or a pharmaceutically acceptable salt or ester thereof, wherein:
$R^1$ and $R^2$ are the same and are from $C_{6-24}$ alkyl or alkenyl; and
Q is a cationic charged head group.

The novel cationic lipid is a lysine amide cationic lipid. This novel cationic lipid has long fatty chains and a cationic charged head group which can be categorized into three groups based on the chemical structures of the head group. The three different head groups represented by formula II are 1) bis-imidoamide head groups; 2) head groups having two to 8 amino groups generated from propylamino repeat units; and 3) head groups having varied numbers of lysl residues linked by amide bonds through alpha or epsilon amino groups in asymmetric and symmetric configurations.

These new cationic lipids are micelle-forming lipids in their salt form and have excellent DNA condensation abilities and capability of forming small complexes with DNA. In vitro test revealed that most of these lipids have high transfection activity on cells in general. However, the two lipids belonging to group three, with three to five lysine groups symmetrically and spaciously distributed over the molecules are 2 to 5 times more potent than those lipids with similar numbers of lysine groups distributed in dendritic (tree) shape or linear pattern. These novel compounds clearly demonstrate the important relationship of structure and transfection activity of a cationic lipid.

Another aspect of the invention relates to cationic lipid compounds of formula II:

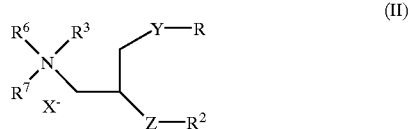

or a pharmaceutically acceptable salt or ester thereof, wherein:

$R^1$ and $R^2$ are the same or different and are from $C_6$ to $C_{24}$ alkyl or alkenyl;

Y and Z are both —O—, or —O—C(O)—; or when one of Y or Z is —O—C(O)—, the other is —O—;

$R^3$ is $C_{1-6}$ alkyl or alkene, aryloxy, aryl, a protecting group, or is absent;

$R^6$ and $R^7$ are taken together with the N atom to form a 5 to 8-membered heterocyclic ring;

$X^-$ is a halogen anion or is absent; and the N atom has a positive charge or is neutral.

Another aspect of the invention relates to a compound of formula IIa:

or a pharmaceutically acceptable salt or ester thereof, wherein:

$R^1$ and $R^2$ are the same or different and are from $C_1$ to $C_{23}$ alkyl or alkenyl, aryl or heterocyclic;

$R^6$ and $R^7$ are taken together with the N atom to form a 5 to 8-membered heterocyclic ring; and $X^-$ is a halogen anion.

Another aspect of the invention relates to a compound of formula (IIb):

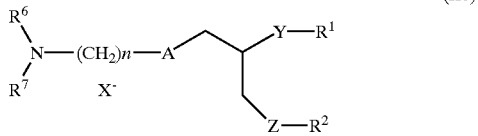

$R^1$ and $R^2$ are the same or different and are from $C_6$ to $C_{24}$ alkyl or alkenyl or aryl;

Y and Z are both —O— or —O—C(O)—;

$R^6$ and $R^7$ are taken together with the N atom to form a 5 to 8-membered heterocyclic ring in which the heterocyclic N is unsubstituted or substituted with one $C_{1-3}$ alkyl groups;

A is —C—(O)—O—;

n=1–6; and $X^-$ is a halogen anion or is absent.

Another aspect of the invention relates to the following compounds represented by:

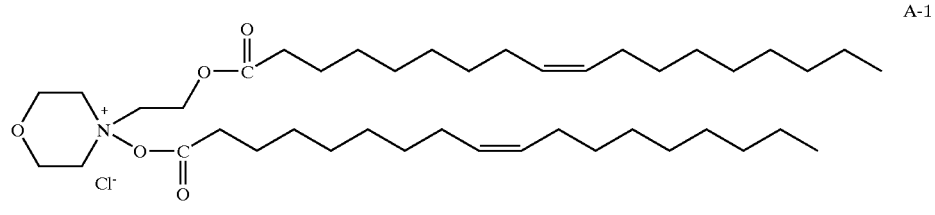

A-1

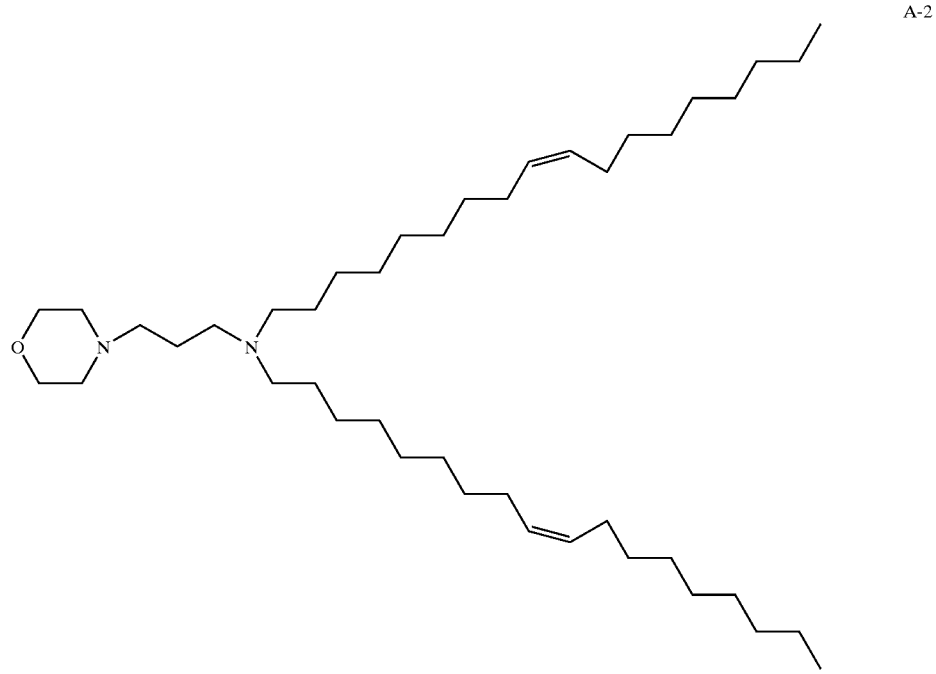

A-2

A-3
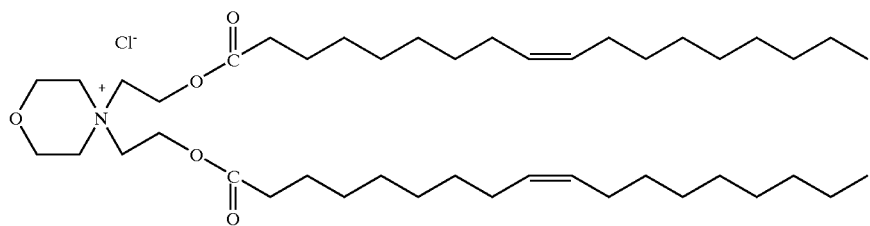
A-4
A-5
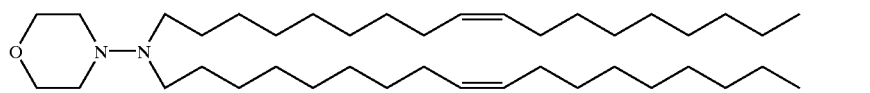
A-6
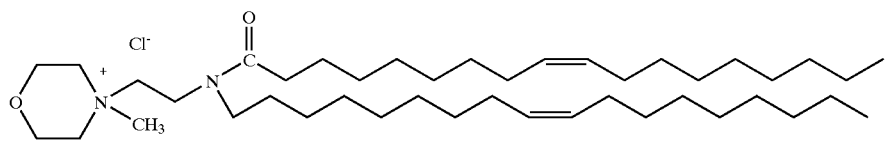
A-7
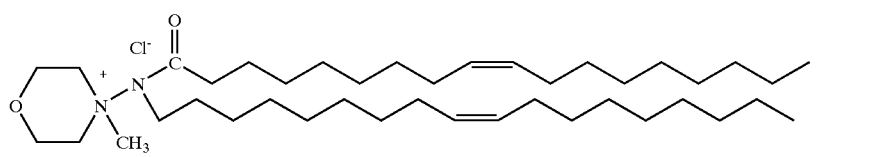
A-8
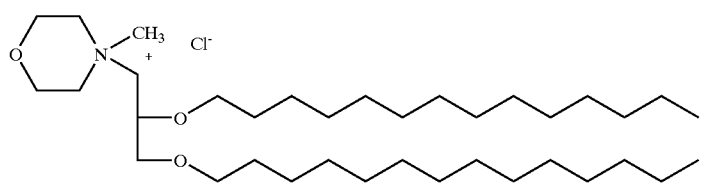
A-9
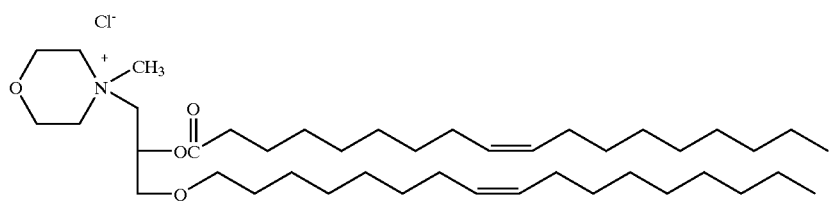
A-10
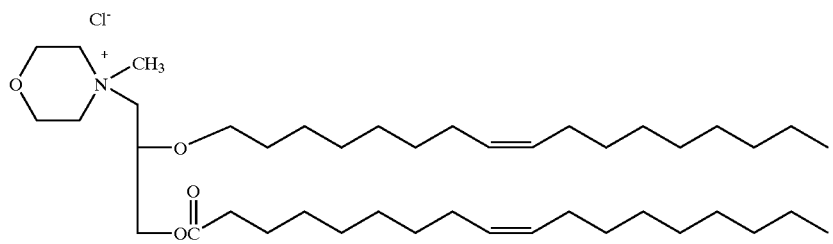

Another aspect of the invention relates to the following compounds represented by:

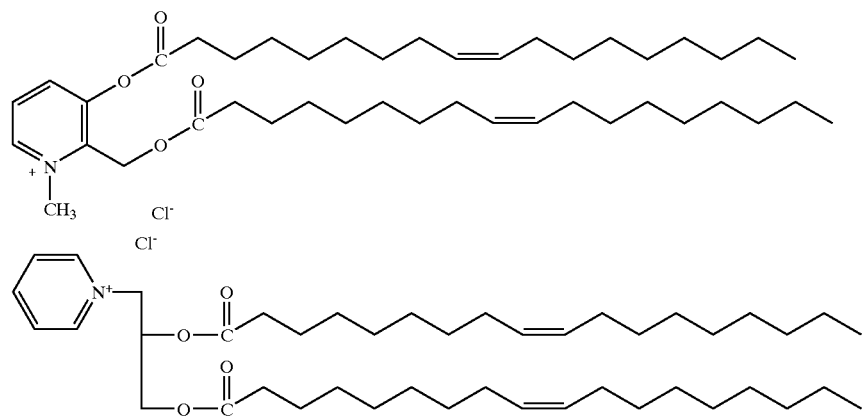

The novel cationic compound is a heterocyclic cationic lipid. Included within this aspect of the invention are several monovalent double chain cationic lipids. Namely, 3-N-methyl-1,2-dioleylpropandiol morpholino chloride (MMET) and 3-N-methyl-1,2-dioleoylpropandiol morpholino chloride (MMES). The novel cationic lipids represented by formula III has a simple ammonium or an ammonium located at the base of a ring structure as a head group which is linked to two long, mono-unsaturated fatty chains as lipid anchors. These lipids contain several types of bonds which link the head groups and lipid anchors, including biodegradable diester bonds, stable diether bonds, alkyl bonds or mixed bonds.

The liposomes composed of a single cationic lipid, or a mixture of cationic lipid and non-charged helper lipids, such as cholesterol at 1:1 ratio, were prepared and used to complex DNA at charge ratios of from 0.75–16±. Liposome/DNA complexes prepared with a plasmid containing a luciferase reporter gene were administered intravenously to mice. After 12 hours, luciferase activity was demonstrated at high levels in lung, liver, spleen and other organs. The magnitude of transgene expression was related the ratio of lipid to DNA and was determined by the lipid composition and the type of helper lipids. For liposomes prepared from single cationic lipids, transgene expression occurred when lipid/DNA ratios reached 1:4 and peaked at ratio of 1:16. Among these lipids, the transfection activity of the compound MMET was much higher than the prior art liposomes composed of DOTMA and/or DOTAP or DOTMA-cholesterol. These prior art complexes caused toxicity to the mice, especially at higher doses.

Another aspect of the invention relates to compounds having the formulas:

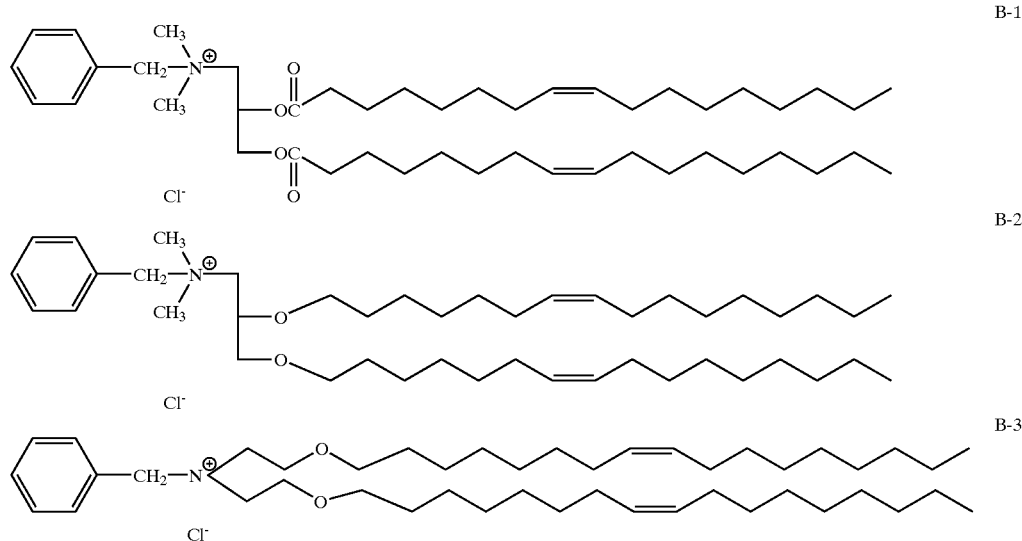

or a pharmaceutically acceptable salt or ester thereof

The novel cationic compound is a benzyl compound. The novel cationic lipid represented has a benzyl group attached to a nitrogen atom, which is linked to two long mono-unsaturated fatty chains as lipid anchors. These lipids contain several types of bonds which link the head groups and lipid anchors, including biodegradable diester bonds, diether bonds, alkyl bonds or mixed bonds.

Another aspect of the relates to cationic compounds having the formulas:

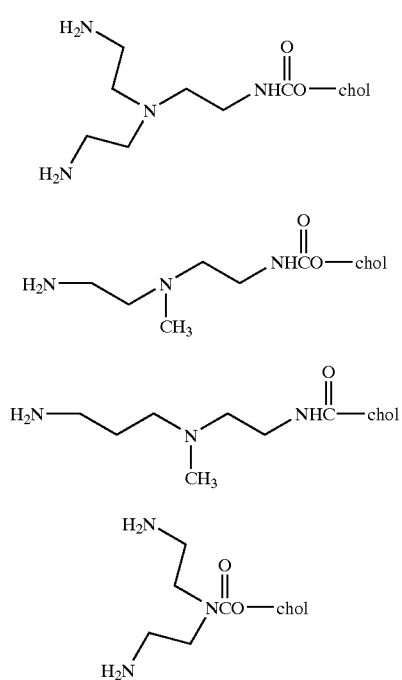

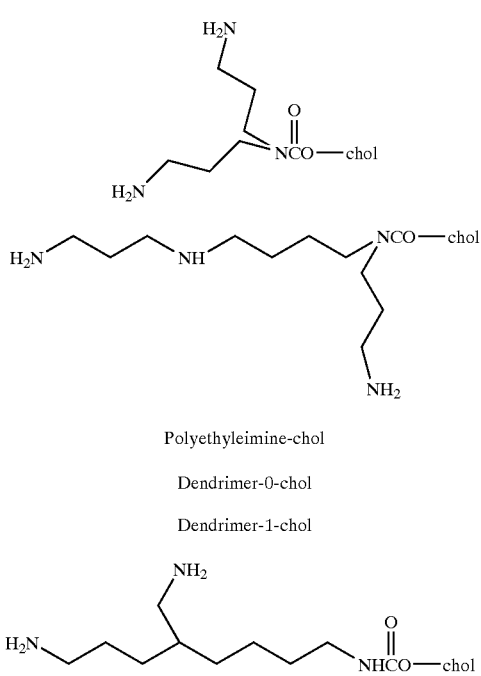

Polyethyleimine-chol

Dendrimer-0-chol

Dendrimer-1-chol

C-1
C-2
C-3
C-4
C-5
C-6
C-7
C-8
C-9
C-10

-continued

 C-11

 C-12

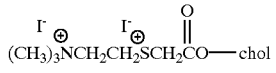 C-13

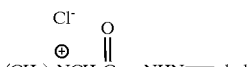 C-14 chol = cholesteryl group or a pharmaceutically acceptable salt or ester thereof.

The novel cationic compound is a cholesterol (or chlolesteryl) containing cationic lipid.

Another aspect of the invention relates to compounds having the formulas:

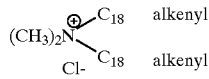 D-1

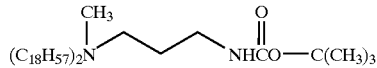 D-2

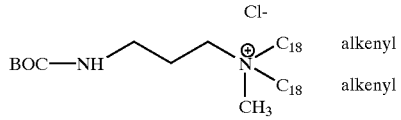 D-3 or a pharmaceutically acceptable salt or ester thereof.

One aspect of the invention relates to compounds having the formulas:

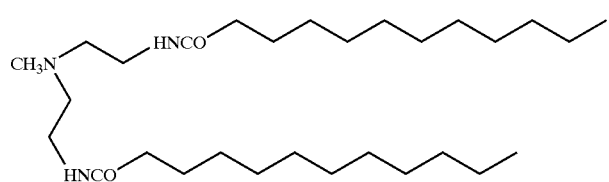 E-1

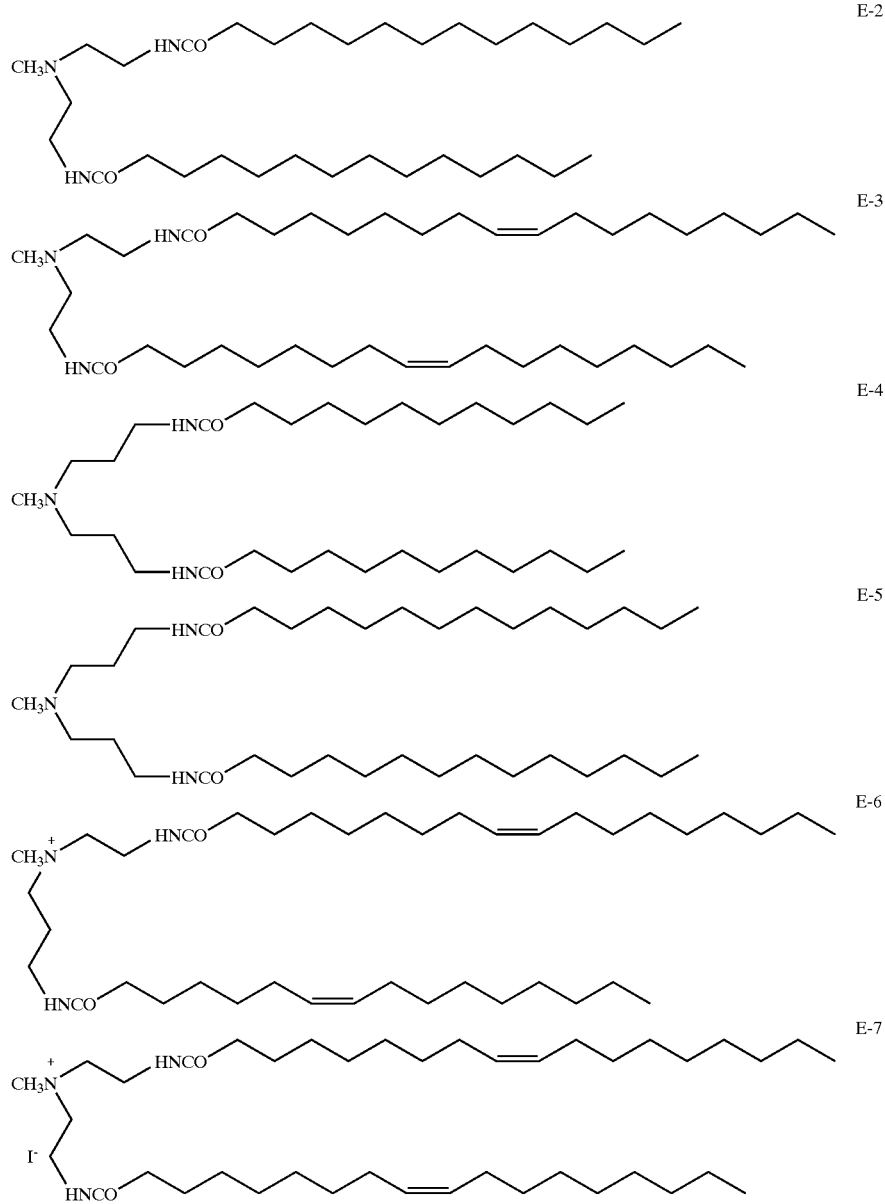
or a pharmaceutical acceptable salt or ester thereof.
One aspect of the invention relates to compounds having the formulas:
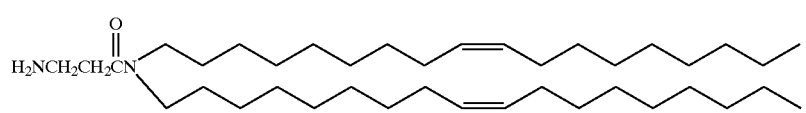
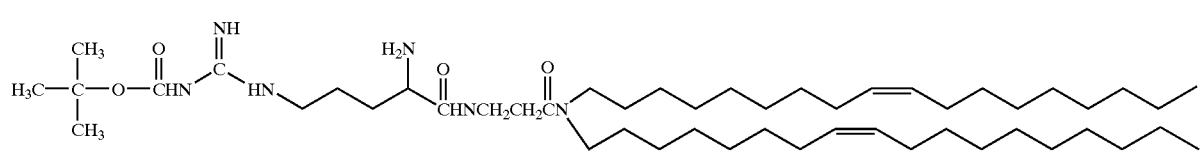
or a pharmaceutically acceptable salt or ester thereof.

One aspect of the invention relates to compounds having the formulas:
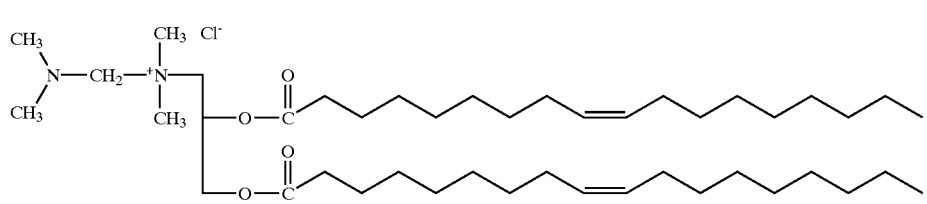
G-1
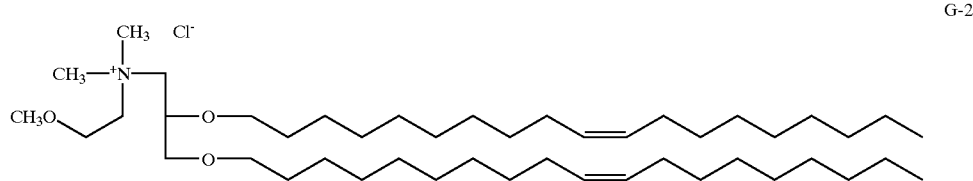
G-2
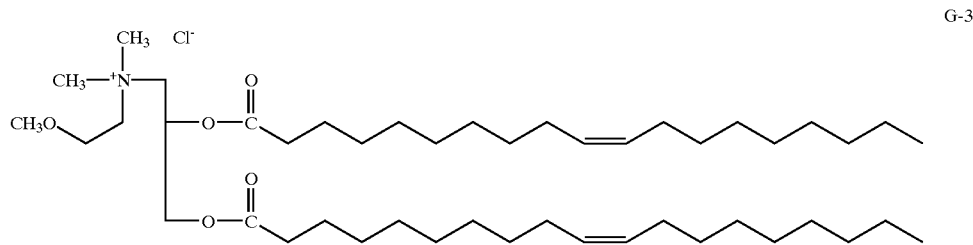
G-3
or a pharmaceutically acceptable salt or ester thereof.
One aspect of the invention relates to a compound of formula IV:
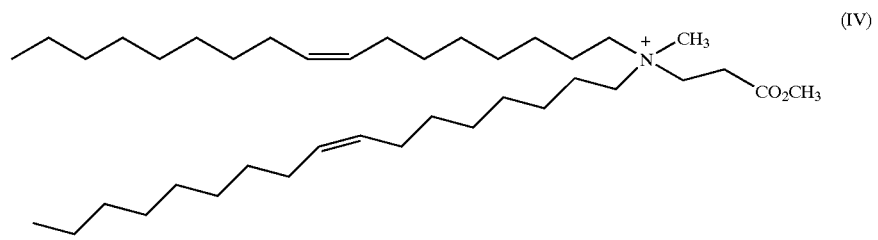
(IV)
or a pharmaceutically acceptable salt or ester thereof.
One aspect of the invention relates to compounds having the formulas:
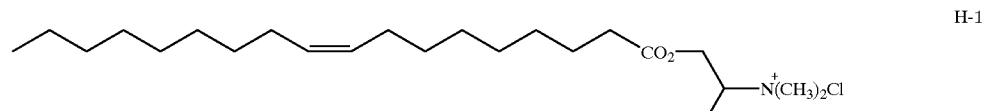
H-1
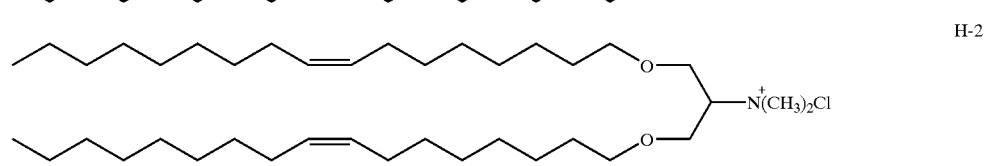
H-2

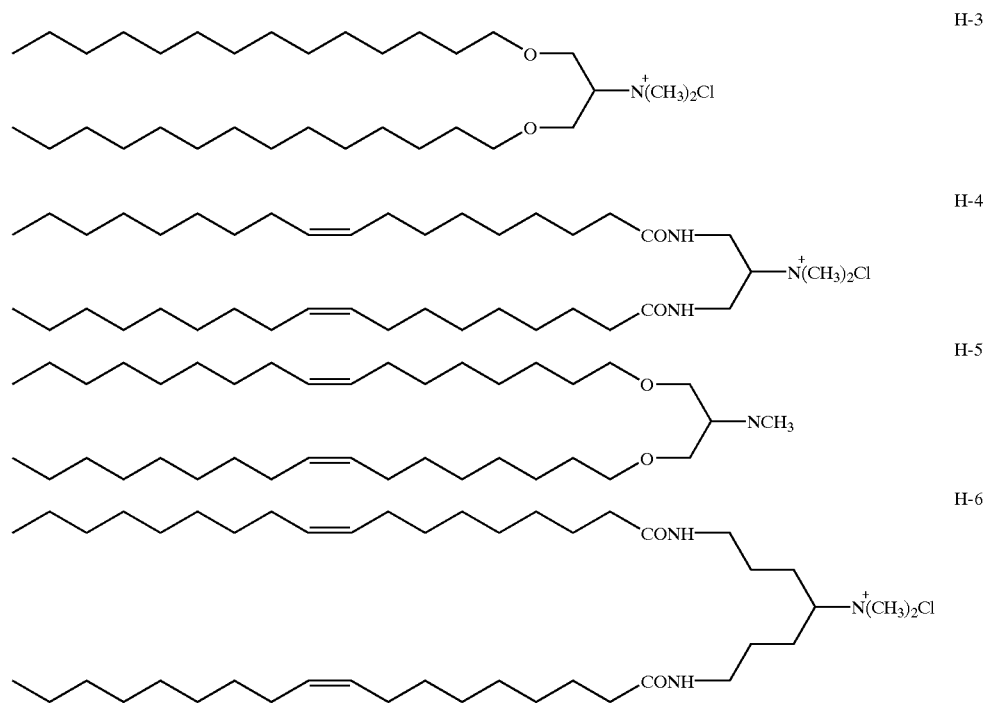
or a pharmaceutically acceptable salt or ester thereof.
One aspect of the invention relates to a compound of formula (V):
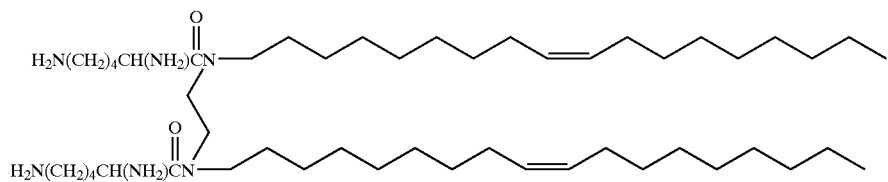
One aspect of the invention relates to compounds having the formulas:
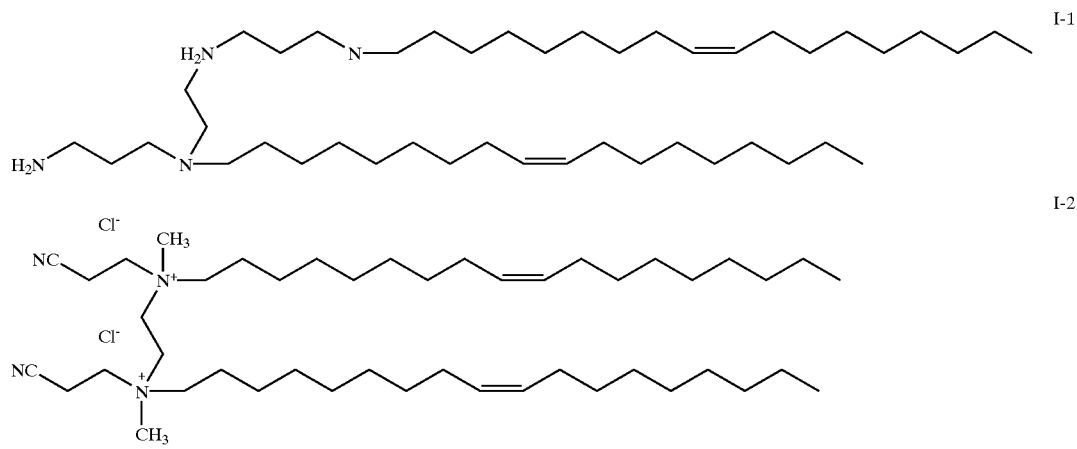

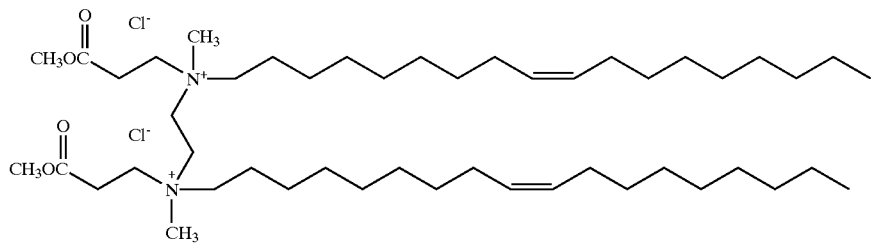
I-3
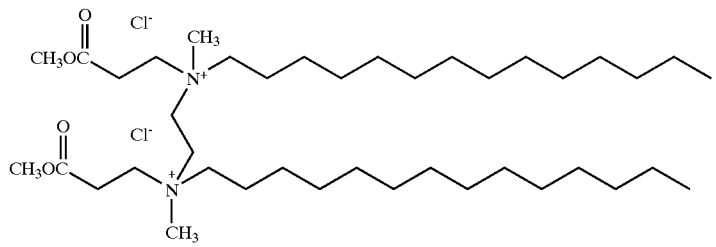
I-4
or a pharmaceutically acceptable salt or ester thereof.
One aspect of the invention relates to compounds having the formulas:
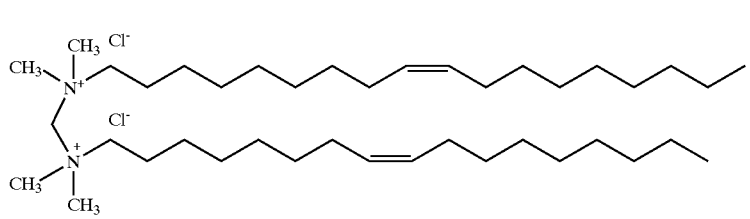
J-1
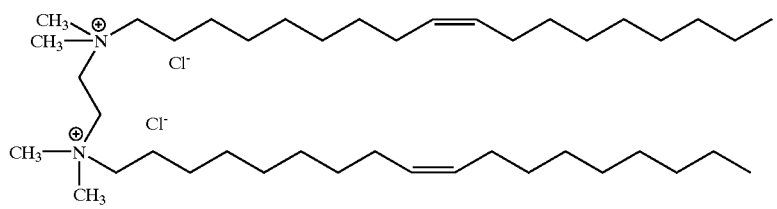
J-2
or a pharmaceutically acceptable salt or ester thereof.
One aspect of the invention relates to compounds having the formulas:
K-1
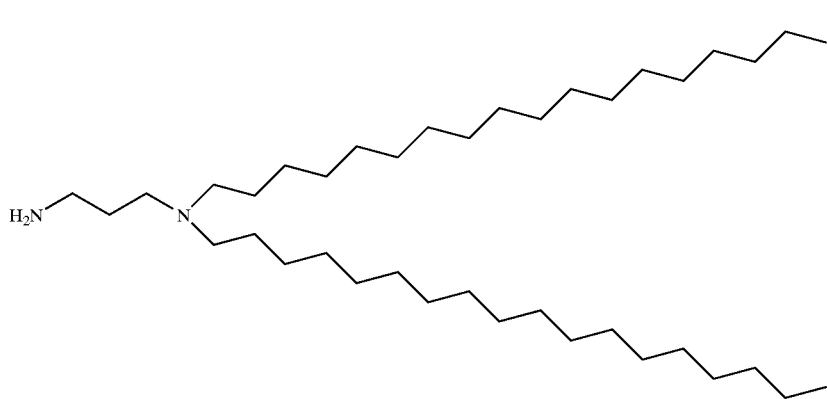

-continued
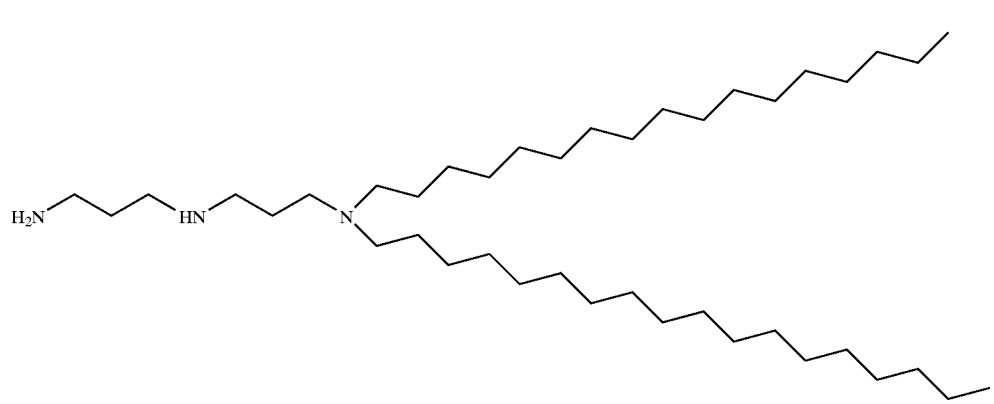
K-2
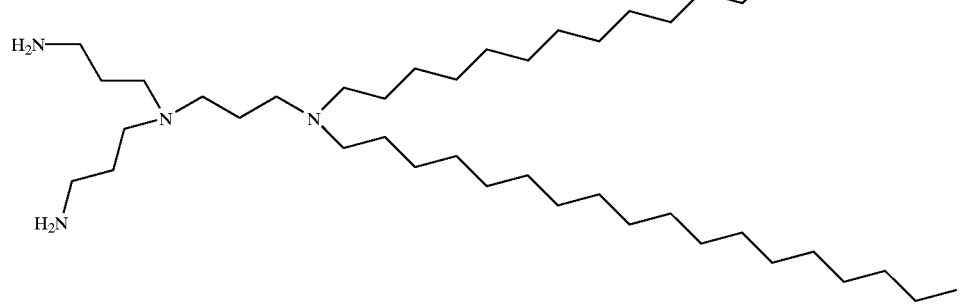
K-3
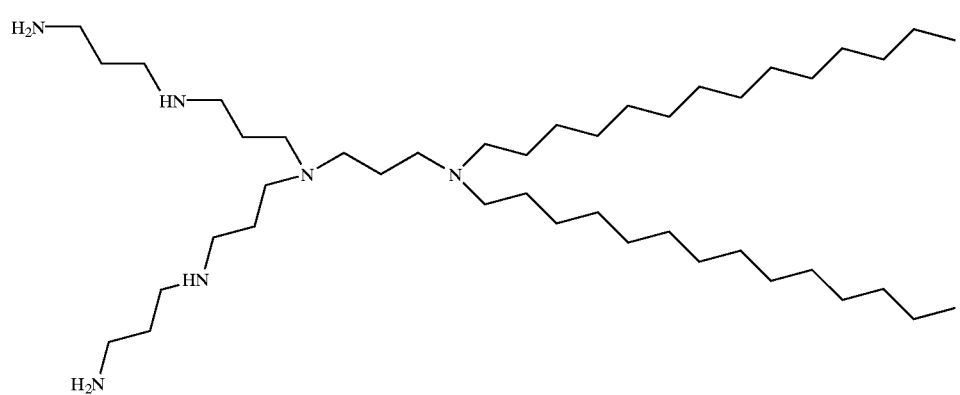
K-4
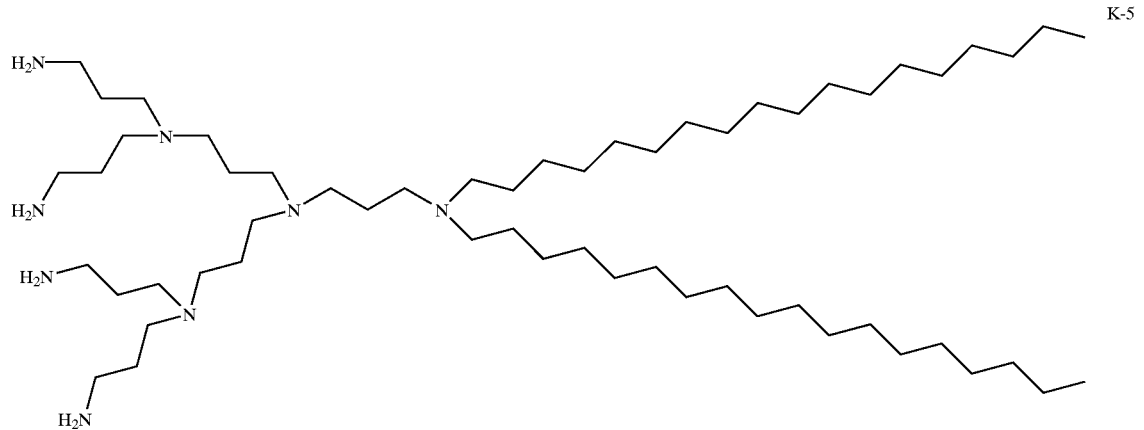
K-5

-continued
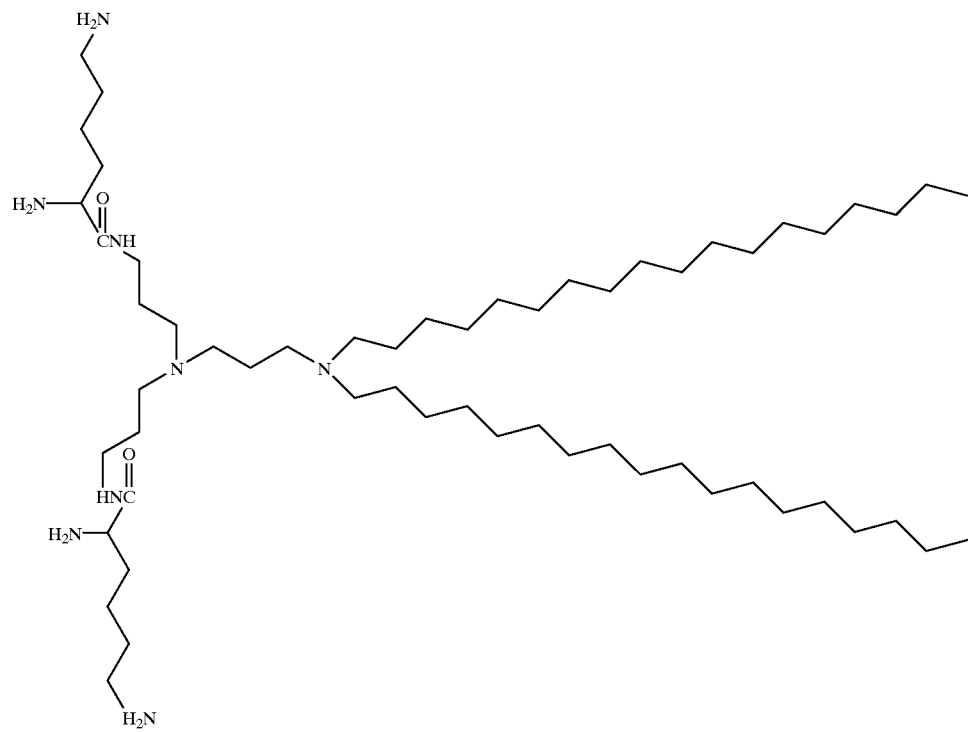
K-6
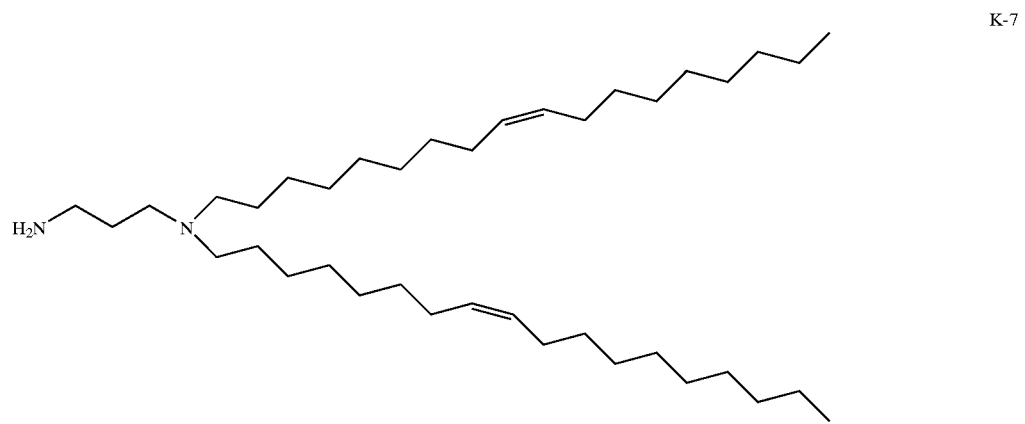
K-7
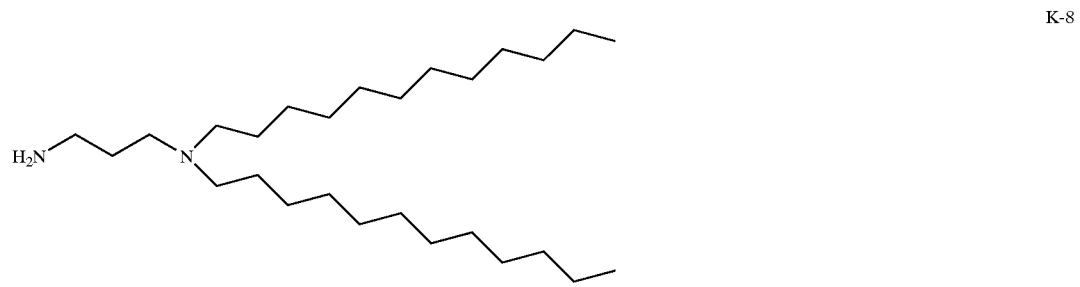
K-8

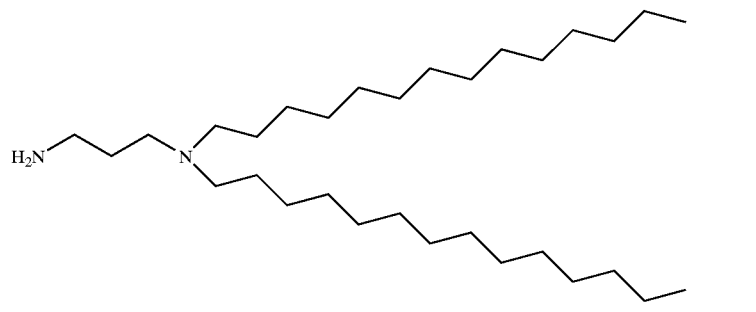
K-9
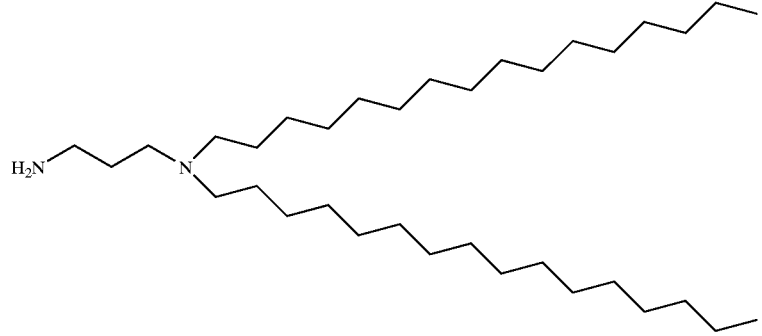
K-10
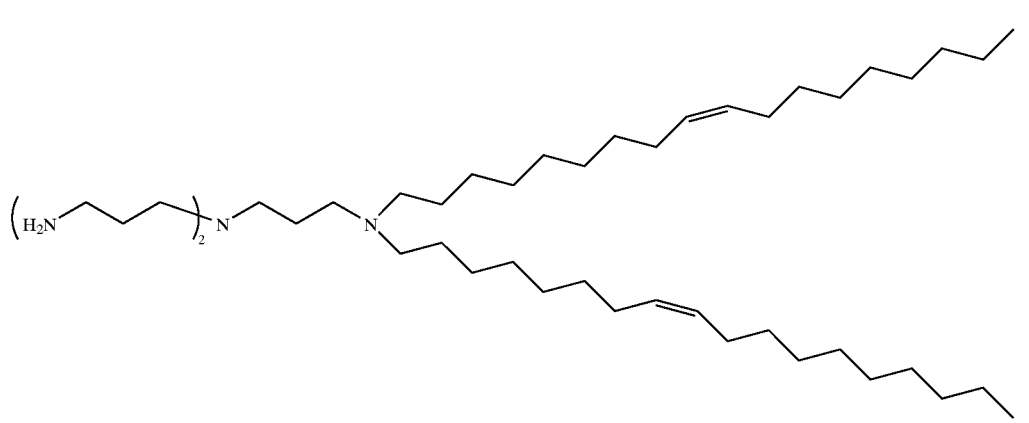
K-11
or a pharmaceutically acceptable salt or ester thereof.
One aspect of the invention relates to compounds having the formulas:
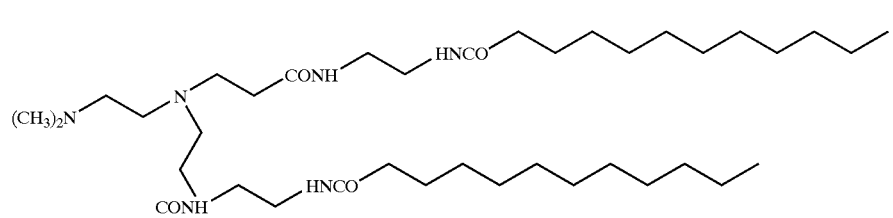
L-1
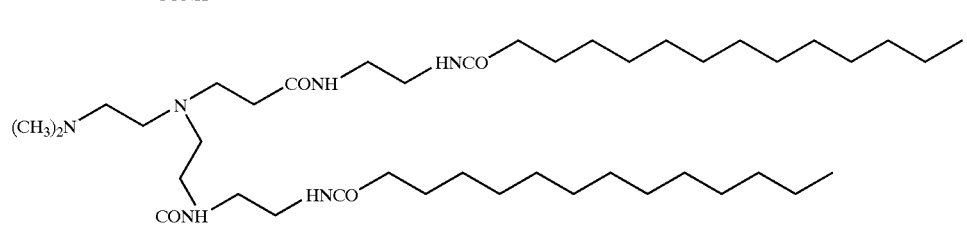
L-2

-continued
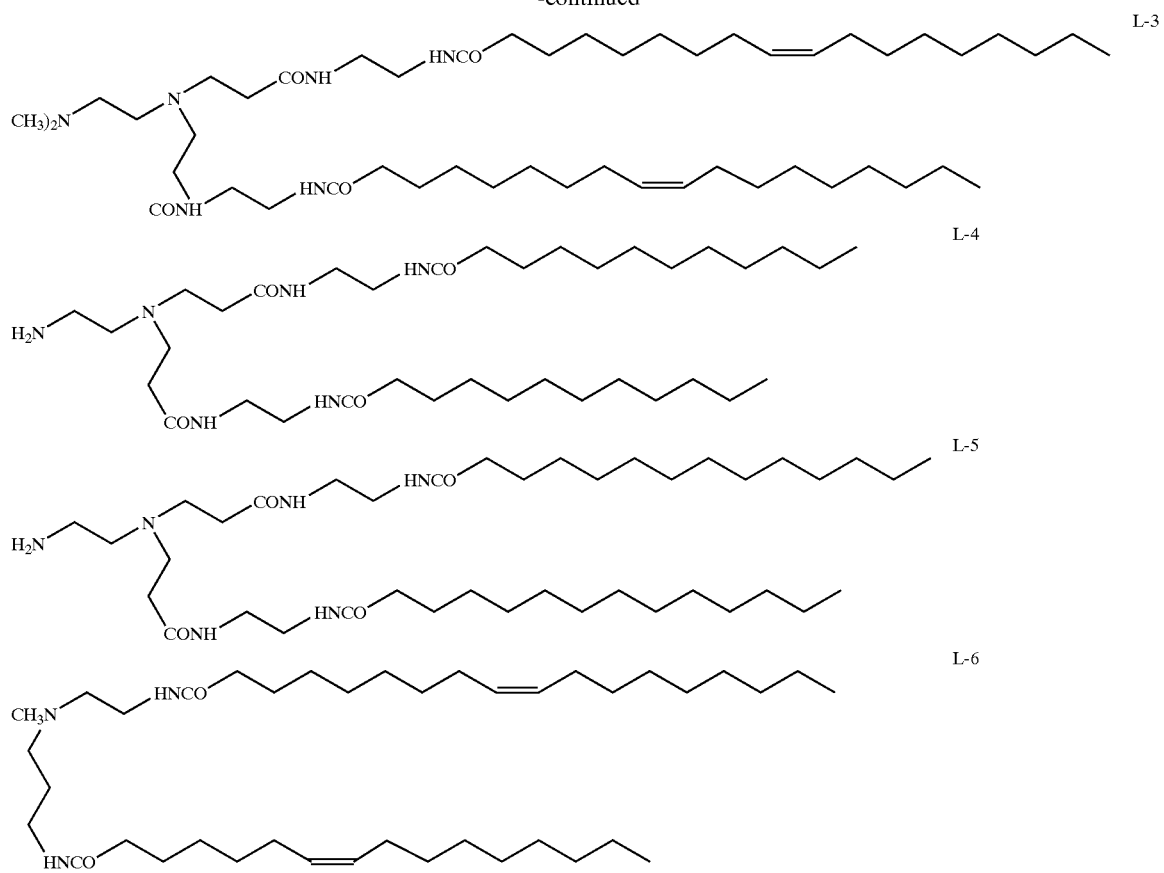
or a pharmaceutically acceptable salt or ester thereof.
Another aspect of the invention relates to compounds having the formulas:
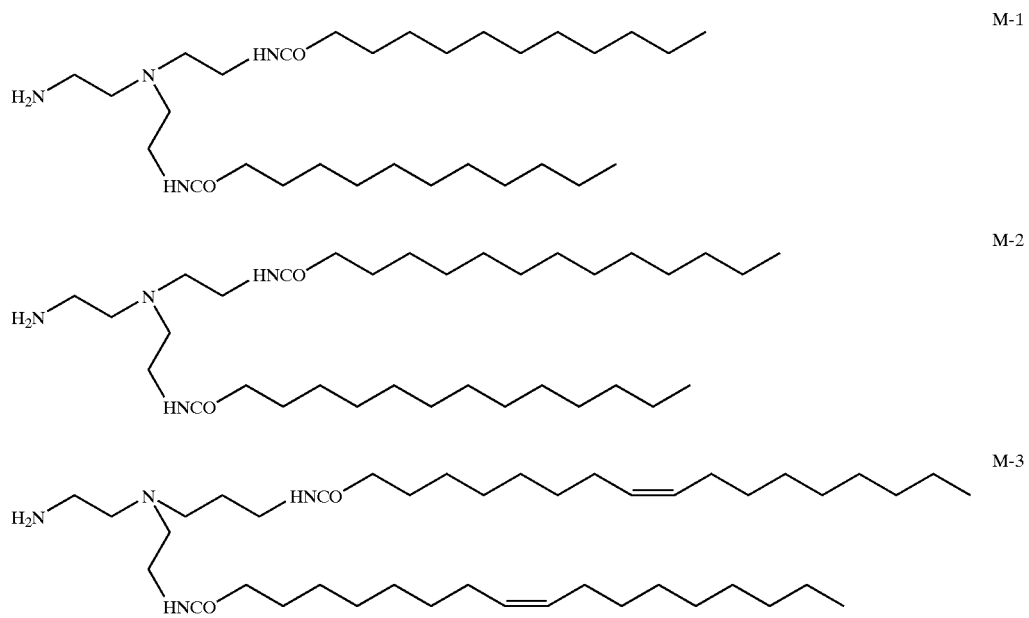
or a pharmaceutically acceptable salt or ester thereof.

One aspect of the invention relates to compounds having the formulas:

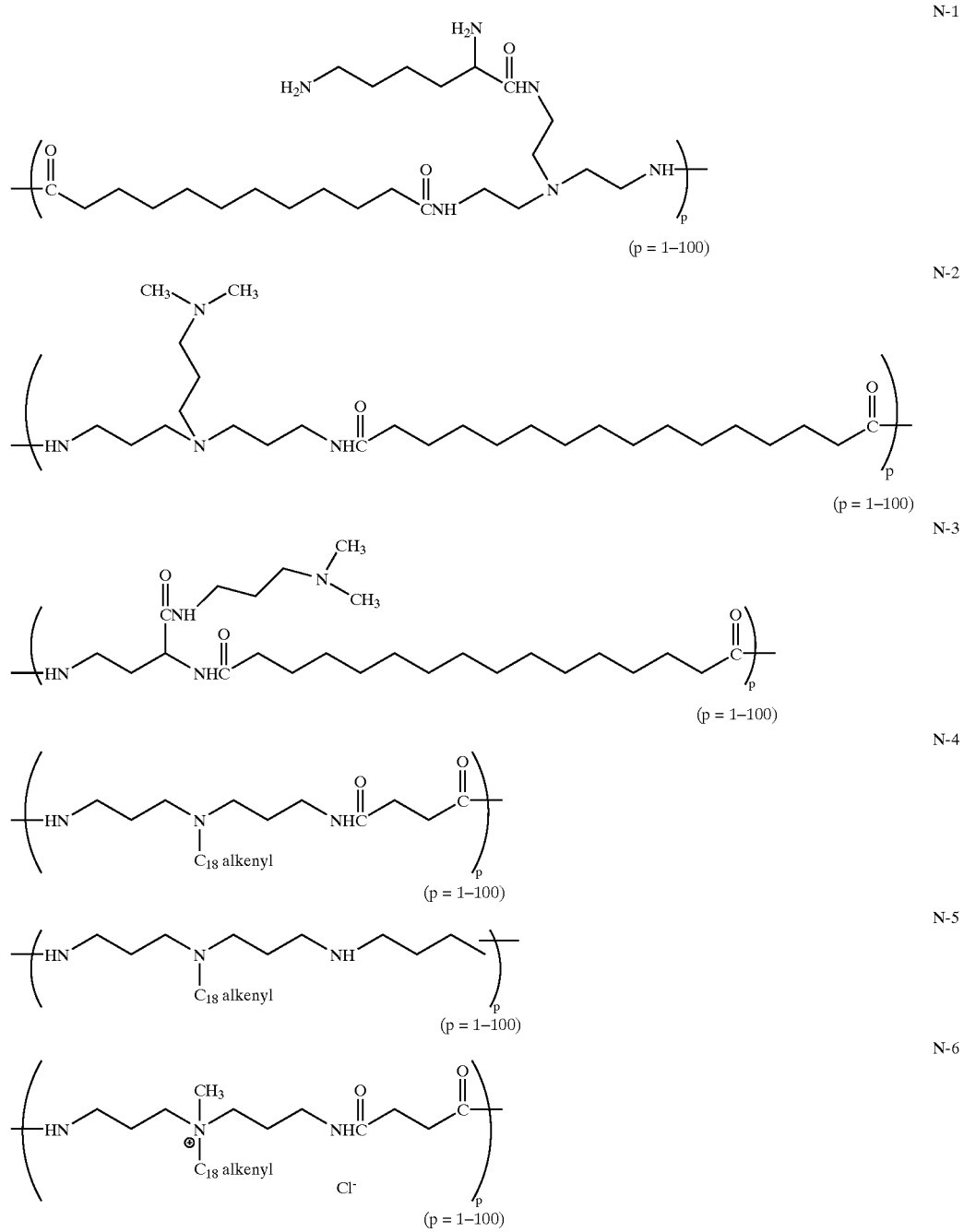

or a pharmaceutically acceptable salt or ester thereof.

Each of these cationic lipids may be used in pharmaceutical formulations in the form of liposomes with a bioactive agent/biologically active agent either alone or in combination with other lipid substituents.

In another aspect, the invention relates to pharmaceutical compositions comprising the aforementioned inventive compounds in combination with a pharmaceutically acceptable carrier. Examples of pharmaceutically acceptable carriers include aqueous solutions and complex delivery systems as further described herein. Preferably, the pharmacologically acceptable carrier is a liposome.

The invention also encompasses pharmaceutically acceptable esters, and salts of such compounds, as will be explained in detail, infra.

Additional advantages of the invention will be set forth in part in the description which follows, and in part will be obvious from the description, or may be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

The accompanying drawings, which are incorporated in and constitute a part of this specification, illustrate several embodiments of the invention and together with the description, serve to explain the principles of the invention.

DETAILED DESCRIPTION OF THE INVENTION

Figure 1:
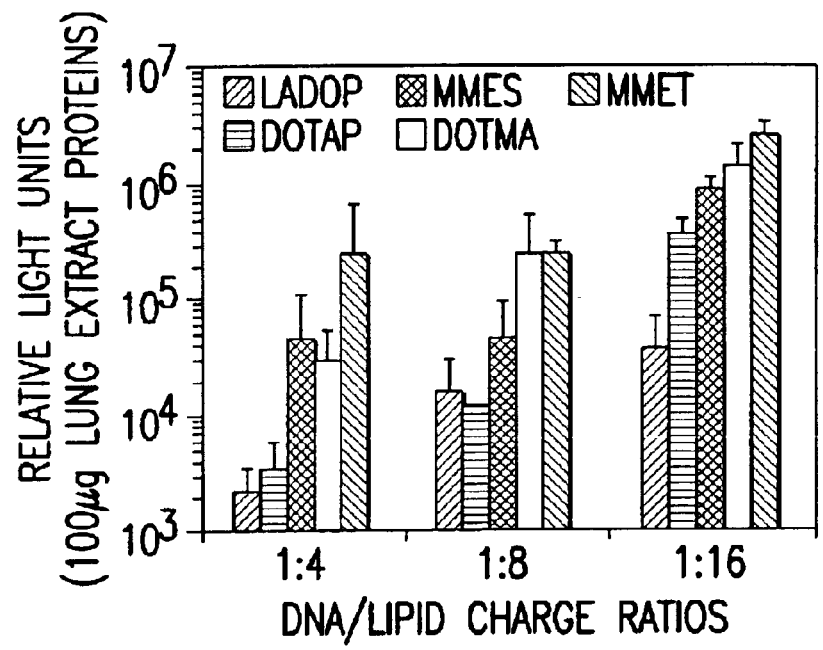
FIG. 1 shows the effects of different DNA/Lipid charge ratios on transfection.

The present invention may be understood more readily by reference to the following detailed description of preferred embodiments of the invention and the Examples included therein and to the Figures and their previous and following description.

Before the present compounds, compositions and methods are disclosed and described, it is to be understood that this invention is not limited to specific synthetic methods, specific pharmaceutical carriers, or to particular pharmaceutical formulations or administration regimens, as such may, of course, vary. It is also to be understood that the terminology used herein is for the purpose of describing particular embodiments only and is not intended to be limiting.

It must be noted that, as used in the specification and the appended claims, the singular forms "a," "an" and "the" include plural referents unless the context clearly dictates otherwise. Thus, for example, reference to "a pharmaceutical carrier" includes mixtures of two or more such carriers, and the like.

Ranges are often expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment.

In this specification and in the claims which follow, reference will be made to a number of terms which shall be defined to have the following meanings:

References in the specification and concluding claims to parts by weight, of a particular element or component in a composition or article, denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent of a component, unless specifically stated to the contrary, is based on the total weight of the formulation or composition in which the component is included.

The term "alkyl" as used herein refers to a branched or unbranched saturated hydrocarbon group of 1 to 24 carbon atoms, such as methyl, ethyl, propyl, n-propyl, isopropyl, n-butyl, isobutyl, t-butyl, octyl, decyl, tetradecyl, hexadecyl, eicosyl, tetracosyl and the like. Preferred alkyl groups herein contain from 1 to 23 carbon atoms.

The term "alkenyl" as used herein refers to a branched or unbranched unsaturated hydrocarbon containing from 2 to 24 carbon atoms and at least one carbon to carbon double bond.

The term "aryl" refers to aromatic rings, e.g., phenyl, substituted phenyl and the like as well as rings which are fused, e.g., napthyl, phenanthrenyl and the like. An aryl group thus contains at least one ring having at least 6 atoms, with up to five such rings being present, containing up to 22 atoms therein, with alternating (resonating) double bonds between adjacent carbon atoms or suitable heteratoms. The preferred aryl groups are benzyl, tolyl or phenyl.

The term "aryloxy" refers to aryl-O—. A preferred aryloxy is carbobenzyloxy.

The term "fatty long chain" herein refers to a branched or unbranched saturated or unsaturated hydrocarbon chain of alkyl groups containing from 1–24 carbon atoms. Preferred "fatty long chains" contain from 4 to 18 carbons.

By the term "effective amount" of a compound as provided herein is meant a nontoxic but sufficient amount of the compound to provide the desired regulation of gene expression. As will be pointed out below, the exact amount required will vary from subject to subject, depending on the species, age, and general condition of the subject, the severity of the disease that is being treated, the particular compound used, its mode of administration, and the like. Thus, it is not possible to specify an exact "effective amount." However, an appropriate effective amount may be determined by one of ordinary skill in the art using only routine experimentation.

By "pharmaceutically acceptable" is meant a material that is not biologically or otherwise undesirable, i.e., the material may be administered to an individual along with the selected compound without causing any undesirable biological effects or interacting in a deleterious manner with any of the other components of the pharmaceutical composition in which it is contained.

The terms "lipoplex" and "liposome complex" have the same meaning herein and are used interchangeably.

The terms "lipofection" and "transfection" have the same meaning herein and are used interchangeably.

The term halogen and "halo" refer to bromine, chlorine, fluorine and iodine.

The term "heterocyclic ring" refers to a monocyclic aromatic having 5 to 8 ring atoms, or a bicyclic aromatic group having 8 to 10 atoms, containing a at least one heteroatom, O, S, or N, in which a carbon or heteroatom is the point of attachment. Examples of preferred heterocyclic rings are pyrrole and morpholine.

The term "heteroatom" means O, S or N selected on an independent basis. The invention also encompasses pharmaceutically acceptable nontoxic ester, amide, and salt derivatives of those compounds of formula (I) containing a carboxylic acid moiety.

The term "protecting group" means that the group is in its modified form to preclude undesired side reactions at the protected site. Suitable protecting groups for the compounds of the present invention will be recognized from the present application taking into account the level of skill in the art, and with reference to standard textbooks, such as Green, T. W., et al., Protective Groups in Organic Synthesis, Wiley, New York (1991). A preferred protecting group in this invention is t-butoxycarbonyl ("BOC").

Pharmaceutically acceptable salts are prepared by treating the free acid with an appropriate amount of a pharmaceutically acceptable base. Representative pharmaceutically acceptable bases are ammonium hydroxide, sodium hydroxide, potassium hydroxide, lithium hydroxide, calcium hydroxide, magnesium hydroxide, ferrous hydroxide, zinc hydroxide, copper hydroxide, aluminum hydroxide, ferric hydroxide, isopropylamine, trimethylamine, diethylarnine, triethylamine, tripropylamine, ethanolamine, 2-dimethylaminoethanol, 2-diethylaminoethanol, lysine, arginine, histidine, and the like. The reaction is conducted in water, alone or in combination with an inert, water-miscible organic solvent, at a temperature of from about 0° C. to about 100° C., preferably at room temperature. The molar ratio of compounds of structural formula (I) to base used are chosen to provide the ratio desired for any particular salts. For preparing, for example, the ammonium salts of the free acid starting material—a particular preferred embodiment— the starting material can be treated with approximately one equivalent of pharmaceutically acceptable base to yield a neutral salt. When calcium salts are prepared, approximately one-half a molar equivalent of base is used to yield a neutral salt, while for aluminum salts, approximately one-third a molar equivalent of base will be used.

Ester derivatives are typically prepared as precursors to the acid form of the compounds—as illustrated in the examples below—and accordingly may serve as prodrugs. Generally, these derivatives will be lower alkyl esters such as methyl, ethyl, and the like. Amide derivatives —(CO)NH$_2$, —(CO)NHR and —(CO)NR$_2$, where R is lower alkyl, may be prepared by reaction of the carboxylic acid-containing compound with ammonia or a substituted amine.

A subset of compounds of formula (I) which is of interest relates to the following compounds:

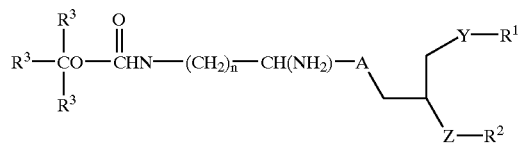

A subset of compounds of formula (Ib) which is of interest relates to:

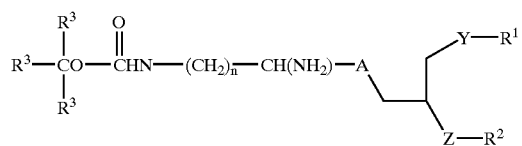

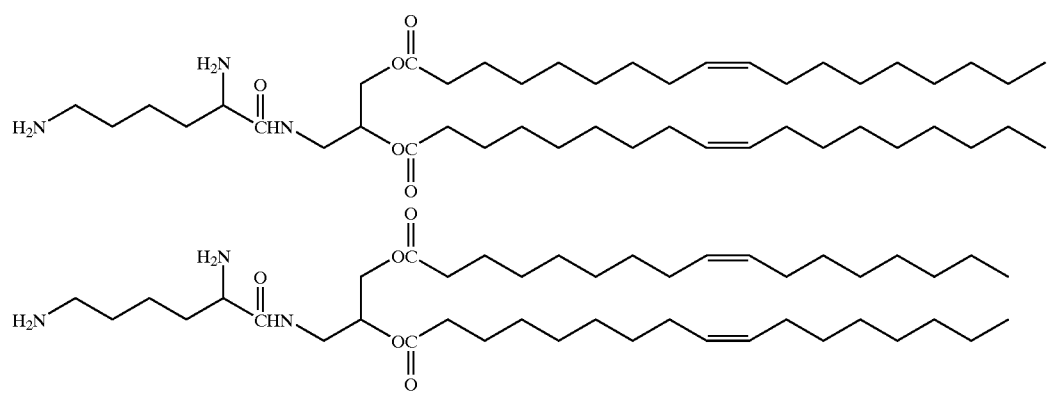

A subset of compounds of formula (Ia) which is of interest relates to:

A subset of compounds of formula (II) which is of interest is represented by formulas:

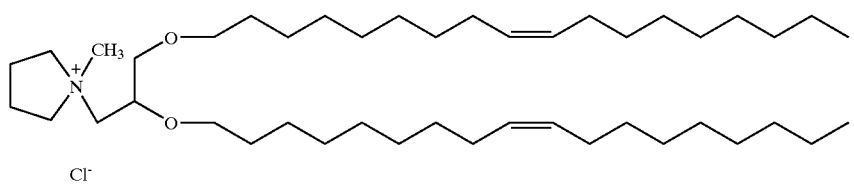

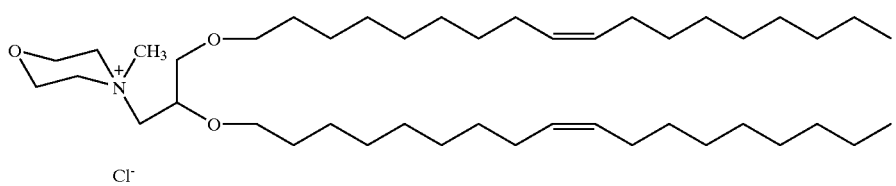

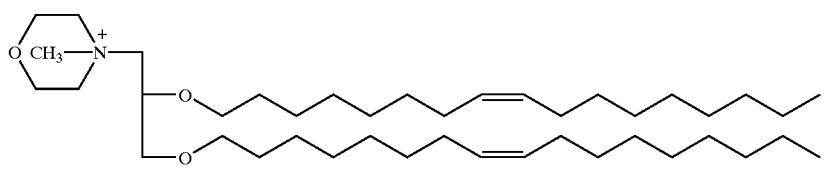

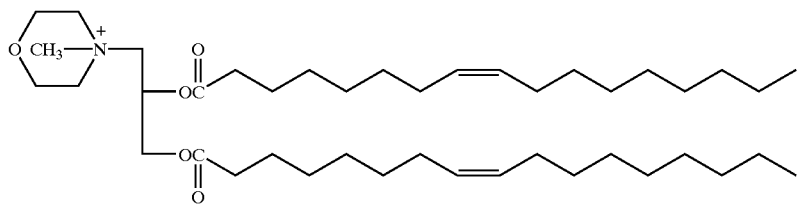

A subset of compounds of formula (IIa) which is of interest is represented by:

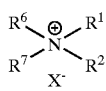
(II(a))

or a pharmaceutically acceptable salt or ester thereof, wherein:
- $R^1$ and $R^2$ are the same or different and are from $C_6$ to $C_{24}$ alkyl or alkenyl or aryl;
- $R^6$ and $R^7$ are taken together with the N atom to form a 5 to 8-membered heterocyclic ring; and
- $X^-$ is a halogen anion.

A subset of formula (IIb) which is of interest is represented by:

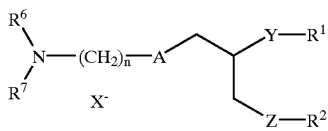
(IIb)

- $R^1$ and $R^2$ are the same or different and are from $C_6$ to $C_{24}$ alkyl or alkenyl or aryl;
- Y and Z are both —O— or —O—C(O)—;
- $R^6$ and $R^7$ are taken together with the N atom to form a 5 to 8-membered heterocyclic ring in which the heterocyclic N is unsubstituted or substituted with one $C_{1-3}$ alkyl groups;
- A is —C—(O)—O—;
- n=1–6; and
- $X^-$ is a halogen anion or is absent.

A subset of compounds of formula (III) which is of interest is represented by the following formulas:

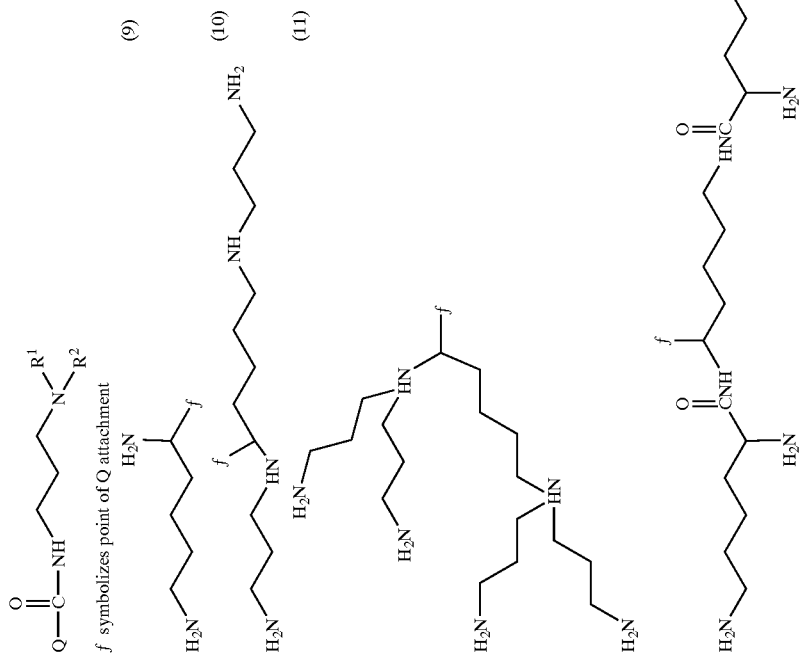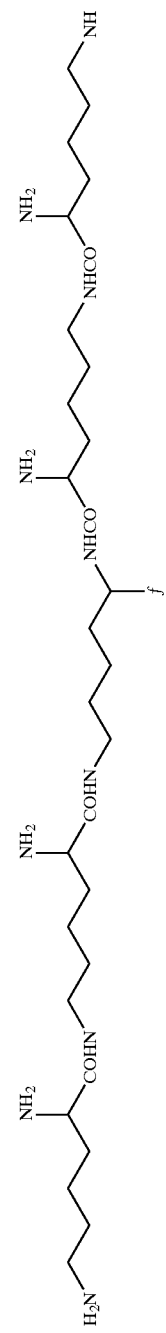

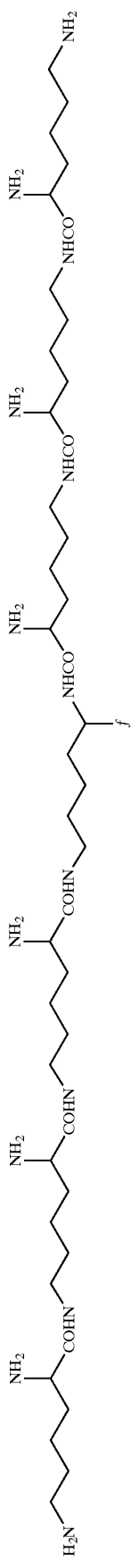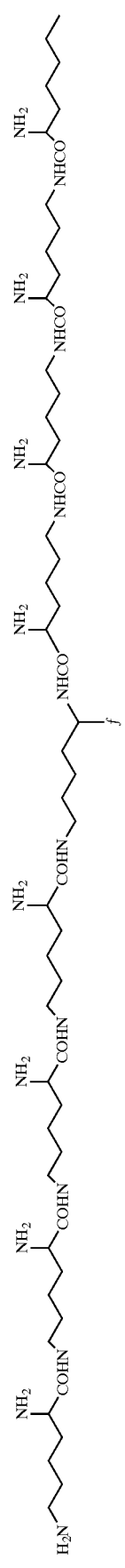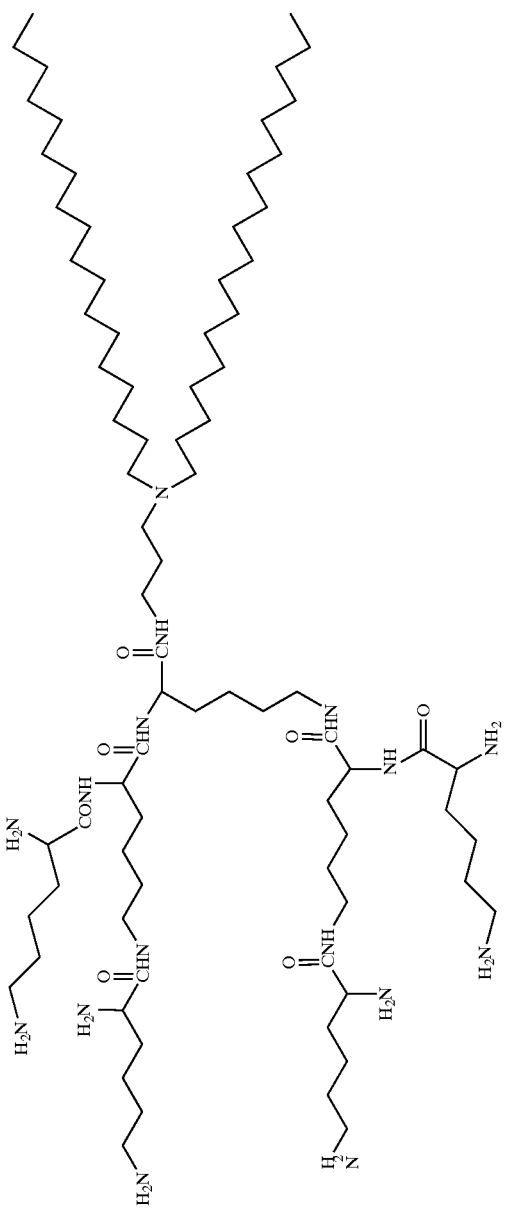

(17)
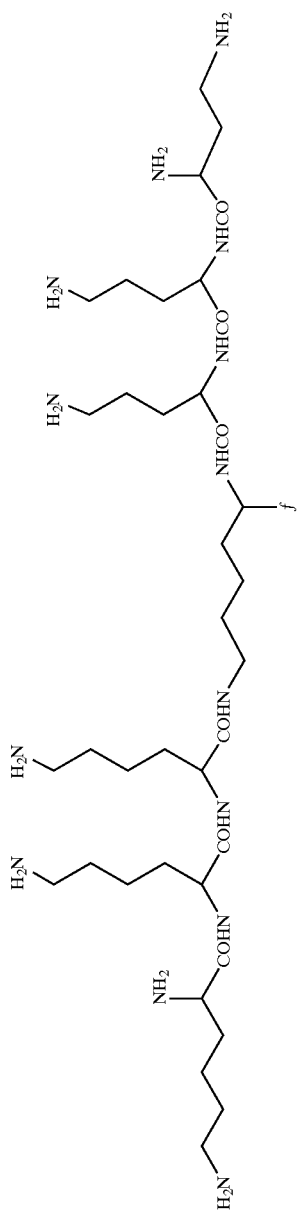
(18)
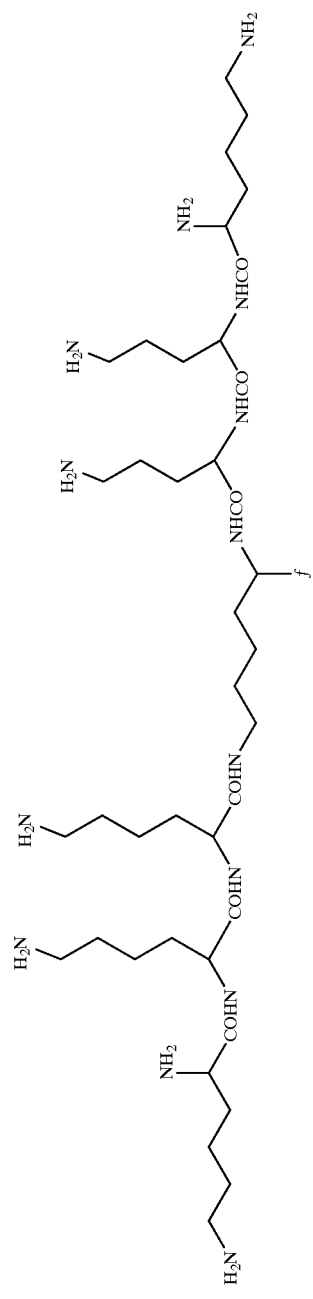
(19)
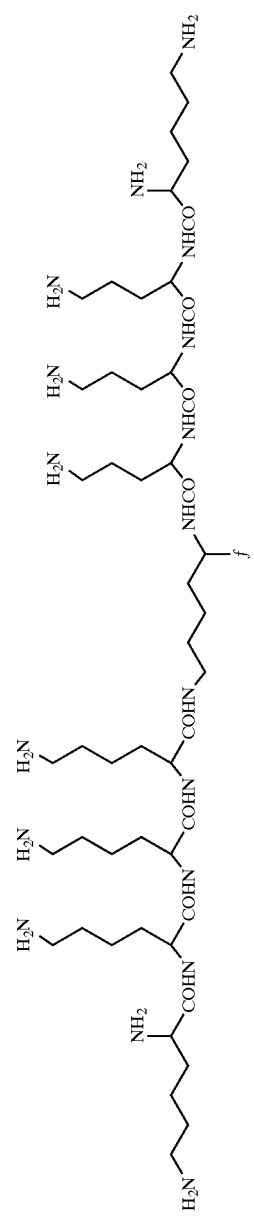

-continued
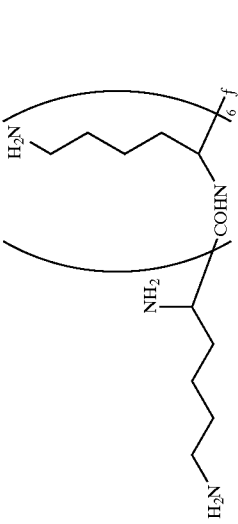
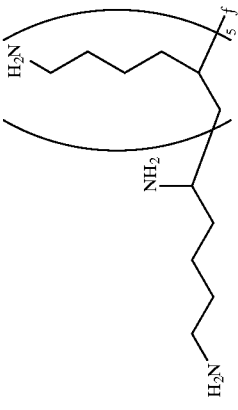

-continued
(26)
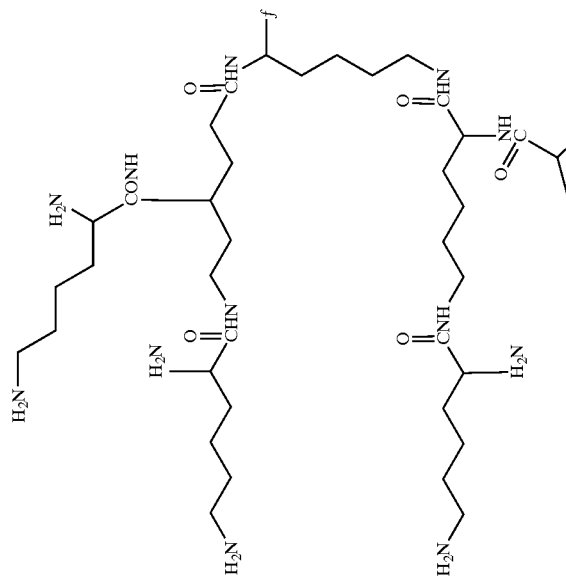
(27)
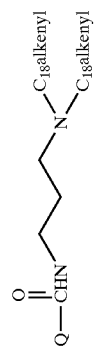
(28)
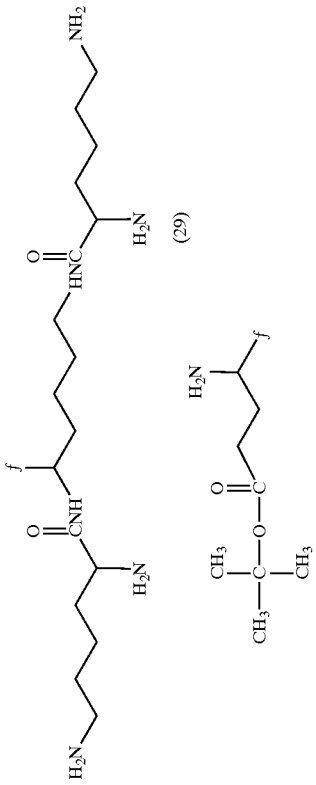
(29)
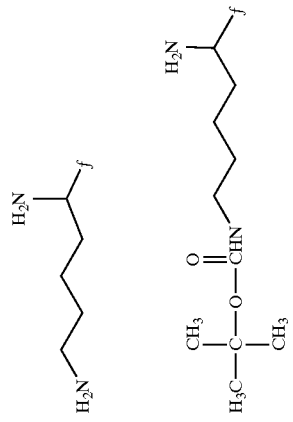

-continued
(31)
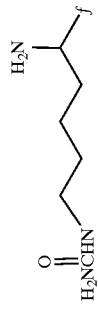
(32)
(33)
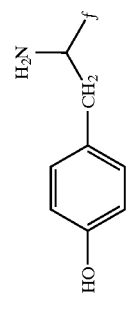
(34)
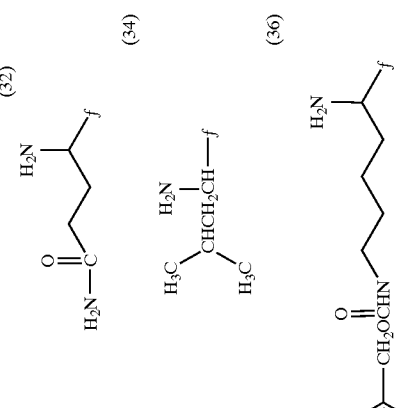
(35)
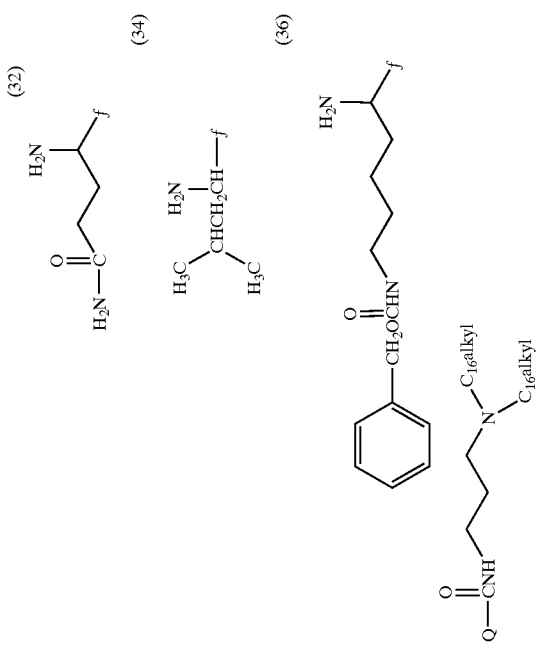
(36)
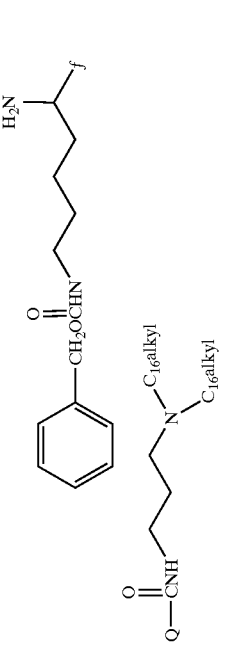
(37)
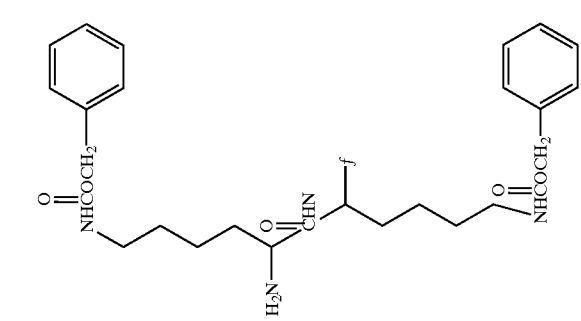

-continued
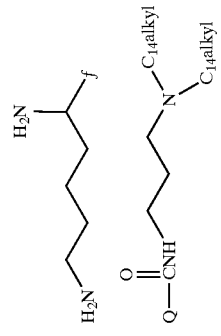
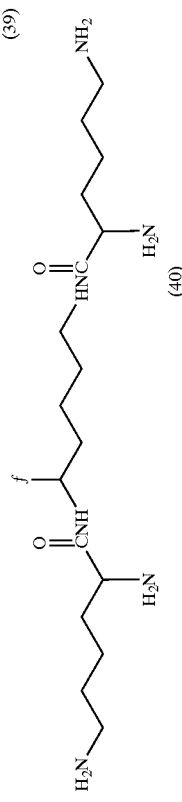
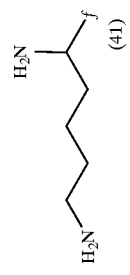
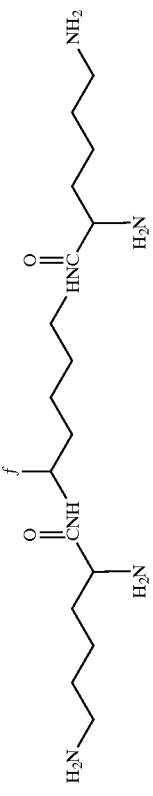
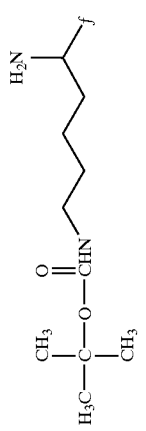
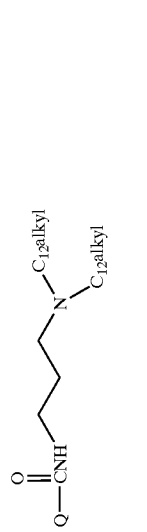
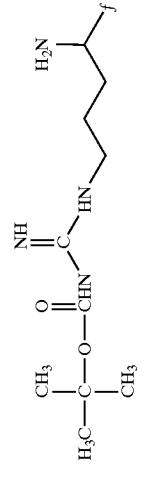
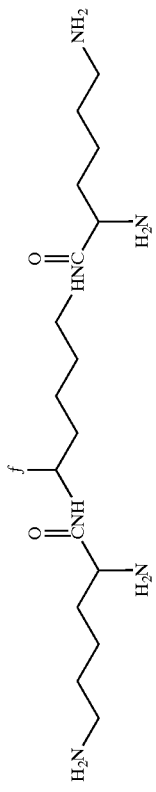
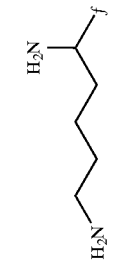

or a pharmaceutically acceptable salt or ester thereof.

Synthetic Methods

The compounds of the invention may be readily synthesized using techniques generally known to synthetic organic chemists. Suitable experimental methods for making and derivatizing aromatic compounds are described, for example, in the references cited in the Background section herein above, the disclosures of which are hereby incorporated by reference for their general teachings and for their synthesis teachings. Methods for making specific and preferred compounds of the present invention are described in detail in Examples below.

Utility and Administration

The compounds of the invention defined by the structures disclosed herein, including the pharmacologically acceptable esters or salts thereof, are useful as transfection agents.

The compounds of the invention may be conveniently formulated into pharmaceutical compositions composed of one or more of the compounds in association with a pharmaceutically acceptable carrier. See, e.g., *Remington's Pharmaceutical Sciences*, latest edition, by E. W. Martin Mack Pub. Co., Easton, Pa., which discloses typical carriers and conventional methods of preparing pharmaceutical compositions that may be used in conjunction with the preparation of formulations of the inventive compounds and which is incorporated by reference herein.

Cationic lipid-mediated transfections can be effectively carried out over a range of cell densities and in a variety of cells. For example transfection into COS.7 cells can be carried out at cell densities from 5,000 cells/well to highly confluent cells at 40,000 cells/well. The successful transfection of highly confluent cells indicates that cell division is not required for either expression or functional delivery of DNA.

The cationic lipids of the invention can be advantageously used, either alone or in combination with other known cationic lipids such as for example, DOTMA or DOTAP, in any procedure comprising the use of liposomes or lipid vesicles to deliver substances intracellularly either in vitro or in vivo. The cationic lipids can also be used in combination with neutral lipids, for example cholesterol. Formulations and methods of formulating lipid vesicles are well known, and examples are provided herein.

Contemplated uses comprise transfection procedures corresponding to those presently known and using amphipathic lipids, including commercial cationic lipid preparations, such as Lipofectin™, and using conventional cationic lipid technology and methods. Accordingly, the lipid compositions disclosed herein can be used to facilitate the intercellular delivery of DNA or mRNA sequences coding for therapeutically active polypeptides, as described in detail in U.S. patent applications Ser. Nos. 326,305 and 467,881 which are hereby incorporated by reference. They can be similarly used for the liposomal delivery of the expressed gene product, the polypeptide or protein itself. Thus cationic lipid mediated delivery of DNA and mRNA polynucleotides or proteins can provide therapy for genetic disease by supplying deficient or absent gene products to treat any genetic disease in which the defective gene or its product has been identified, such as Duchenne's dystrophy (Kunkel, L. and Hoffman, E. *Brit. Med. Bull.* 45(3):630–643 (1989) or cystic fibrosis (Goodfellow, P. *Nature,* 341 (6238):102–3 (Sep. 14, 1989).

The cationic lipid-mediated intracellular delivery described above can also provide immunizing polypeptides to the cell, either by delivering a polynucleotide coding for the immunogen, or the immunogen itself.

The transfection procedures described herein may be carried out by direct injection of cationic lipids together with DNA, RNA or proteins into cells of an animal in vivo. However, it has been recently shown that cationic lipids are particularly effective at facilitating in vitro transfection of cells. Therefore the present therapies can be alternatively carried out by in vitro transfection of some of the cells of an animal using cationic lipid delivery methods, and reintroduction of the cells into the animal. The ability to transfect cells at high efficiency with cationic lipids thus provides an alternate method for immunization. The gene for an antigen is introduced, by means of cationic lipid-mediated delivery, into cells which have been removed from an animal. The transfected cells, now expressing the antigen, are reinjected into the animal where the immune system can now respond to the antigen. The process can be enhanced by co-injection of either an adjuvant or lymphokines, or a gene coding for such lymphokines, to further stimulate the lymphoid cells.

Other therapeutically important polynucleotides suitable for cationic lipid mediated delivery are negatively charged novel oligonucleotides including antisense polynucleotide sequences, useful in eliminating or reducing the production of a gene product, as described by Tso, P. et al. *Annals New York Acad. Sci.* 570:220–241 (1987). Many of these oligonucleotide species are inefficiently captured by encapsulation into liposomes of negatively charged lipids, according to ordinary current methods. These oligonucleotides are captured within the present cationic liposomes with efficiencies approaching 100%. Also within the scope of the invention is the delivery, by means of the cationic lipids disclosed, of ribozymes, or catalytic RNA species, either of the "hairpin" type as described by Hampel et al. *Nucleic Acids Research* 18(2):299–304 (1990; or the "Hammerhead" type described by Cech. T. and Bass, B. *Annual Rev. Biochem.* 55:599–629 (1986). These antisense nucleic acids or ribozymes can be expressed (replicated) in the transfected cells.

The DNA sequences used in these methods can be those sequences which do not integrate into the genome of the host cell or those which do integrate into the genome of the host. These may be non-replicating DNA sequences, or specific replicating sequences genetically engineered to lack the genome-integration ability.

Therapeutic polynucleotides provided by the invention can also code for immunity-conferring polypeptides, which can act as endogenous immunogens to provoke a humoral or cellular response, or both. The polynucleotides employed according to the present invention can also code for an antibody. In this regard, the term "antibody" encompasses whole immnunoglobulin of any class, chimeric antibodies and hybrid antibodies with dual or multiple antigen or epitope specificities, and fragments, such as F(ab)$_2$, Fab$^1$, Fab and the like, including hybrid fragments. Also included within the meaning of "antibody" are conjugates of such fragments, and so-called antigen binding proteins (single chain antibodies) as described, for example, in U.S. Pat. No. 4,704,692, the contents of which are hereby incorporated by reference.

Thus, an isolated polynucleotide coding for variable regions of an antibody can be introduced in accordance with the present invention, to enable the treated subject to produce antibody in situ. For illustrative methodology relating to obtaining antibody-encoding polynucleotides, see Ward et al. *Nature,* 341:544–546 (1989); Gillies et al., *Biotechnol.*

7:799–804 (1989); and Nakatani et al., loc. Cit., 805–810 (1989). The antibody in turn would exert a therapeutic effect, for example, by binding a surface antigen associated with a pathogen. Alternatively, the encoded antibodies can be anti-idiotypic antibodies (antibodies that bind other antibodies) as described, for example, in U.S. Pat. No. 4,699,880. Such anti-idiotypic antibodies could bind endogenous or foreign antibodies in a treated individual, thereby to ameliorate or prevent pathological conditions associated with an immune response, e.g., in the context of an autoimmune disease.

The invention provides the delivery of either an antisense polynucleotide or ribozyme as described above, and having as its target the rev site of the HIV genome (*Scientific American*, October, 1988, pp. 56–57). Matsukura, M. et al. *Proc. Nat'l Acad Sci.* 86:4244–4248 (1989) describe a 28-mer phosphorothioate compound anti-HIV (anti-rev transactivator) specific for the site. Other antisense molecules include those targeted to essential genes of other pathogens, or to genes of the subject that express a detrimental product.

Where the polynucleotide is to be DNA, promoters suitable for use in various vertebrate systems are well known. For example, for use in murine systems, suitable strong promoters include RSV LTR, MPSV LTR, SW40 IEP, and metallothionein promoter. In humans, on the other hand, promoters such as CMV IEP may advantageously be used. Cell specific promoters can also be used to permit expression of the gene only in the target cell. For example, certain genes are highly promoted in adults only in particular types of tumors. Similarly, tissue-specific promoters for specialized tissue, e.g., lens tissue of the eye, have also been identified and used in heterologous expression systems. All forms of DNA, whether replicating or non-replicating, and which are expressible, are within the methods contemplated by the invention.

With the availability of automated nucleic acid synthesis equipment, both DNA and RNA can be synthesized directly when the nucleotide sequence is known or by a combination of PCR cloning and fermentation. Moreover, when the sequence of the desired polypeptide is known, a suitable coding sequence for the polynucleotide can be inferred.

When the polynucleotide is mRNA, it can be readily prepared from the corresponding DNA in vitro. For example, conventional techniques utilize phage RNA polymerases SP6, T3, or T7 to prepare mRNA from DNA templates in the presence of the individual ribonucleoside triphosphates. An appropriate phage promoter, such as T7 origin of replication site is placed in the template DNA immediately upstream of the gene to be transcribed. Systems utilizing T7 in this manner are well known, and are described in the literature, e.g., in Current Protocols in Molecular Biology, § 3.8 (vol. 1, 1988).

In addition, the present invention includes the use of mRNA that is chemically blocked at the 5' and/or 3' end to prevent access by RNASE. (This enzyme is an exonuclease and therefore does not cleave RNA in the middle of the chain.) Such chemical blockage can substantially lengthen the half life of the RNA in vivo. Two agents which may be used to modify RNA are available from Clonetech Laboratories, Inc., Palo Alto, Calif.: C2 Amino Modifier (Catalog #5204-1) and Amino-7-dUTP (Catalog #K1022-1). These materials add reactive groups to the RNA. After introduction of either of these agents onto an RNA molecule of interest, an appropriate reactive substituent can be linked to the RNA according to the manufacturer's instructions. By adding a group with sufficient bulk, access to the chemically modified RNA by RNASE can be prevented.

Therapeutic uses of cationic lipids herein disclosed include the liposomal delivery of nucleoside or nucleotide analogues having an antiviral effect, such as dideoxynucleotides, didehydronucleotides, nucleoside or nucleotide analogues having halo-substituted purine or pyrimidine rings such as 5-trifluoromethyl-2'-deoxyuridine or 5-flurouracil; nucleoside or nucleotide analogues having halo- and azido-substituted ribose moieties, such as 3'-azido-3'deoxythymidine (AZT), nucleoside analogues having carbon substituted for oxygen in the ribose moiety (carbocyclic nucleosides), or nucleotide analogues having an acyclic pentose such as acyclovir or gancyclovir (DHPG). The liposomal delivery of such analogues is disclosed in U.S. Patent No. The antiviral potency of these analogues is found to be increased when they are presented to the cells as phospholipid derivatives. These derivatives may be incorporated into the liposomal structure for administration to cells thereby forming a more stable liposomal complex which can deliver greater amounts of drugs to target cells with less toxicity. Effective antiviral lipid derivatives of nucleoside analogues comprise phosphatidyl 2', 3'-dideoxynucleosides, 2'3'-didehydronucleosides, 3'-azido-2'-deoxynucleosides, 3'-fluorodeosynucleosides and 3'-fluorodideoxynucleosides, 9-β-D-arabinofuranosyladenine (araA), 1-β-D-arabinofuranosylcytidine (araC), nucleosides such as acyclovir and gancyclovir having an acyclic ribose group, or the same nucleoside analogues as diphosphate diglyceride derivatives. Preferred species of lipid derivatives of antiviral or antiretroviral nucleoside analogues for the treatment of HIV infection using cationic lipid mediated liposomal delivery are phospholipid derivatives of 3'-halopyrimidine dideoxynucleoside, or a 2',3'-didehydro-2',3'-dideoxynucleoside, for example, phosphatidyl 3'-azido-3'deoxythymidine (pAZT) or phosphatidyl 2-chlorodeoxyadenosine. Certain viral infections, comprising herpes, cytomegalovirus, and hepatitis B infections are effectively treated with nucleoside analogues comprising acyclovir, gancyclovir, 1-(2-deoxy-2'-fluoro-1-β-D-arabinofuranosyl)-5-iodouracil (FIAU). Phospholipid derivatives of these agents, preferably the phosphatidyl and diphosphate diglyceride derivatives can be administered in these diseases using cationic lipid liposomal delivery systems, according to the invention. Details of the structures, synthesis and liposomal delivery of lipid derivatives of antiviral nucleosides are presented in U.S. patent application Ser. Nos. 216,412; 319,485; and U.S. Pat. No. 5,223,263 which are hereby incorporated by reference.

Among other therapeutically important agents that can be thus delivered are peptides comprising physiologic species such as interleukin-2, tumor necrosis factor, tissue plasminogen activator, factor VIII, erythropoietin, growth factors such as epidermal growth factor, growth hormone releasing factor, neural growth factor, and hormones such as tissue insulin, calcitonin, and human growth hormone as well as toxic peptides such as ricin, diphtheria toxin, or cobra venom factor, capable of eliminating diseased or malignant cells.

Use of the disclosed lipids is also contemplated for the encapsulation of various other agents to be delivered intracellularly according to methods known to those skilled in the art, and as described in Duzgunes, N., *Subcellular Biochemistry* 11:195–286 (1985). Materials to be delivered can be proteins or polypeptides, especially negatively charged molecules, monoclonal antibodies, RNA-stabilizing factors and other transcription and translation regulating factors, antisense oligonucleotides, ribozymes, and any molecule possessing intracellular activity. Such encapsulation further protects the described agents from non-productive sequestration by substances of the extracellular environment.

Several classes of drugs consisting of small organic molecules can be delivered in the formulations as described above. One such class comprises steroidal anti-inflammatory agents which may be prepared in liposomal formulations for topical application. Drugs of this class comprise hydrocortisone, fluocinolone acetonide, available as Synalar™ (Syntex, Palo Alto, Calif. 94303); fluocinonide, available as Lidex™ (Syntex, Palo Alto, Calif. 94303); and dexamethasone, available as Decaderm™ (Merck, Sharpe and Dohme, West Point, Pa. 19486).

Another group of drugs that can be delivered orally, topically, or systemically with the cationic lipid materials according to formulations of the invention are non-steroidal anti-inflammatory agents, such as, for example, 1-acetylsalicylic acid (aspirin; Bayer); piroxicam, available as Feldene® (Pfizere, New York, N.Y. 10017); (Z)-5-fluoro-2-methyl-1-[[p-alcohol(methylsulfinyl)phenyl]methylene] 1-H-indene-3-acetic acid (sulindac), available as Clinoril™ (Merck, Sharpe and Dohme, West Point, Pa. 19486); 2-[(2, 6-dichloropheny-1)amino]benzeneacetic acid, monosodium salt (diclofenae), available as Voltaren™ (Ciba-Geigy, Summit, N.J.); 2',4'-difluoro-4-hydroxy-3-biphenylcarboxylic acid (diflunisal), available as Dolobid™, (Merck, Sharpe and Dohme); (±)-2-(p-isobutylphenyl) propionic acid (ibuprofen), available as Advil™ (Whitehall Laboratories, Inc., New York, N.Y. 10017); N-(2), 6-dichloro-m-tolyl) anthranilic acid )meclophenomate), available as Meclomen™ (parke-Davis, Morris Plains, N.J. 07950; fenoprofen, an arylacetic acid derivative, available as Nalfon™ (Dista Products Co., Indianapolis, Ind. 46285; 2-naphthaleneacetic acid, 6-methoxy-alpha-methyl-, (+) (naproxyn), available as Naprosyn™ (Syntex, Palo Alto, Calif. 94303); 1-methyl-5-(4-methylbenzoyl)-1H-pyrrole-2-acetate dihydrate (tolmetin), available as Tolectin™ (McNeil Pharmaceutical, Spring House, Pa. 19477); and derivatives and congeners thereof.

The cationic lipids of the invention can be used in pharmaceutical formulations to deliver therapeutic agents by various routes and to various sites in the animal body to achieve a desired therapeutic effect. Local or systemic delivery of the therapeutic agent can be achieved by administration comprising application or insertion of the formulation into body cavities, inhalation or insulation of an aerosol, or by parenteral introduction, comprising intramuscular, intravenous, intradermal, peritoneal, subcutaneous and topical administration. The polynucleotides may be delivered to the interstitial space of tissues of the animal body, including those of muscle, skin, brain, lung, liver, spleen, bone marrow, thymus, heart, lymph, blood, bone, cartilage, pancreas, kidney, gall bladder, stomach, intestine, testis, ovary, uterus, rectum, nervous system, eye, gland, and connective tissue. Interstitial space of the tissues comprises the intercellular, fluid, mucopolysaccharide matrix among the reticular fibers of organ tissues, elastic fibers in the walls of vessels or chambers, collagen fibers of fibrous tissues, or that same matrix within connective tissue ensheathing muscle cells or in the lacunae of bone. It is similarly the space occupied by the plasma of the circulation and the lymph fluid of the lymphatic charuels. The effect of the cationic lipids in these formulations is to enhance the potency and efficiency of the therapeutic agent contained therein by facilitating its intracellular delivery.

The present lipocomplexes may be conveniently delivered by injection into the tissues comprising these cells. They are preferably delivered to and expressed in persistent, non-dividing cells which are differentiated, although delivery and expression may be achieved in non-differentiated or less completely differentiated cells, such as, for example, stem cells of blood or skin fibroblasts. In vivo muscle cells are particularly competent in their ability to take up and express polynucleotides. This ability may be due to the singular tissue architecture of muscle, comprising multinucleated cells, sarcoplasmic reticulum, and transverse tubular system. Polynucleotides may enter the muscle through the transverse tubular system, which contains extracellular fluid and extends deep into the muscle cell. It is also possible that the polynucleotides enter damaged muscle cells which then recover.

In all of the administration strategies presented herein, an effective DNA or mRNA dosage will generally be in the range of from about 0.02 $\mu$g/kg to about 100 mg/kg, usually about 0.005–5 mg/kg. However, as will be appreciated, this dosage will vary in a manner apparent to those of skill in the art according to the activity of the peptide coded for by the DNA or mRNA and the particular peptide used. For delivery of adenosine deaminase to mice or humans, for example, adequate levels of translation are achieved with a DNA or mRNA dosage of about 0.5 to 5 mg/kg. From this information, dosages for other peptides of known activity can be readily determined.

Topical formulations are those advantageously applied to the skin or mucosa. Target mucosa can be that of the gastrointestinal tract, comprising the mouth, naso-pharynx and stomach, or the vaginal or anorectal mucosa. Other target tissues can be the accessible surfaces and canal of the ear and the ocular tissues. Cationic lipids present in topical formulations can act to facilitate introduction of bioactive molecules into the target tissue, such as the stratum corneum of the skin, by perturbing the barrier properties of the protective membrane, or by introducing perturbing agents or penetration enhancers such as Azone™ or by promoting the activity of these penetration enhancers. They may also be delivered into muscle or skin using a vaccine gun.

Other topical formulations comprising the cationic lipids are preparations comprising topical antibiotics such as clindamycin, tobramycin, neomycin, gentamycin, tetracycline, erythromycin; oxidants such as benzoyl peroxide, antifungal agents, such as clotrimazole, miconazole, nystatin, lactoconzole, econazole, and tolnaftate; retinoic acid for the treatment of herpes simplex and comprising antiviral nucleoside analogues such as acyclovir and gancyclovir. These nucleoside analogue formulations preferably comprise lipid derivatives of the antiviral agents, particularly the phosphatidylglycerol derivatives as disclosed in U.S. application Ser. No. 373,088, and such may be incorporated into liposomes comprising one or more cationic lipids of the invention.

Other pharmaceutical formulations comprising the cationic lipids of the invention are topical preparations containing an anesthetic or cytostatic agent, immunomodulators, bioactive peptides or oligonucleotides, sunscreens or cosmetics. Preparations for topical use are conveniently prepared with hydrophilic and hydrophobic bases in the form of creams, lotions, ointments or gels; alternatively, the preparation may be in the form of a liquid that is sprayed on the skin. The effect of the cationic lipids is to facilitate the penetration of the active antiviral agent through the stratum corneum of the dermis.

Similar preparations for ophthalmic use are those in which the pharmacologically effective agent is timolol, betaxolol, levobunaloa, pilocarpine, and the antibiotics and corticosteriods disclosed for topical applications.

The composition and form of pharmaceutical preparations comprising the cationic lipids disclosed, in combination with a drug or other therapeutic agent, can vary according to the intended route of administration.

Orally administered preparations may be in the form of solids, liquids, emulsions, suspensions, or gels, or preferably in dosage unit form, for example as tablets or capsules. Tablets may be compounded in combination with other ingredients customarily used, such as talc, vegetable oils, polyols, gums, gelatin, starch, and other carriers. The lipid vesicles may be dispersed in or combined with a suitable liquid carrier in solutions, suspensions, or emulsions.

Parenteral compositions intended for injection, either subcutaneously, intramuscularly, or intravenously, can be prepared with as liquids or solid forms for solution in liquid prior to injection, or as emulsions. Such preparations are sterile, and liquids to be injected intravenously should be isotonic. Suitable excipients are, for example, water, dextrose, saline, and glycerol.

Administration of pharmaceutically acceptable salts of the polynucleotides described herein is included within the scope of the invention. Such salts may be prepared from pharmaceutically acceptable non-toxic bases including organic bases and inorganic bases. Salts derived from inorganic bases include sodium, potassium, lithium, ammonium, calcium, magnesium, and the like. Salts derived from pharmaceutically acceptable organic non-toxic bases include salts of primary, secondary, and tertiary amines, basic amino acids, and the like. For a helpful discussion of pharmaceutical salts, see S. M. Berge et al., Journal of Pharmaceutical Sciences 66:1–19 (1977) the disclosure of which is hereby incorporated by reference.

Polynucleotides for injection, a preferred route of delivery, may be prepared in unit dosage form in ampules, or in multidose containers. The polynucleotides may be present in such forms as suspensions, solutions, or emulsions in oily or preferably aqueous vehicles. Alternatively, the polynucleotide salt may be in lyophilized form for reconstitution, at the time of delivery, with a suitable vehicle, such as sterile pyrogen-free water. Both liquids as well as lyophilized forms that are to be reconstituted will comprise agents, preferably buffers, in amounts necessary to suitably adjust the pH of the injected solution. For any parenteral use, particularly if the formulation is to be administered intravenously, the total concentration of solutes should be controlled to make the preparation isotonic, hypotonic, or weakly hypertonic. Nonionic materials, such as sugars, are preferred for adjusting tonicity, and sucrose is particularly preferred. Any of these forms may further comprise suitable formulatory agents, such as starch or sugar, glycerol or saline. The compositions per unit dosage, wether liquid or solid, may contain from 0.1% to 99% of polynucleotide material.

The units dosage ampules or multidose containers, in which the polynucleotides are packaged prior to use, may comprise an hermetically sealed container enclosing an amount of polynucleotide or solution containing a polynucleotide suitable for a pharmaceutically effective dose thereof, or multiples of an effective dose. The polynucleotide is packaged as a sterile formulation, and the hermetically sealed container is designed to preserve sterility of the formulation until use.

The cationic lipids of the invention may also be present in liquids, emulsions, or suspensions for delivery of active therapeutic agents in aerosol form to cavities of the body such as the nose, throat, or bronchial passages. The ratio of active ingredient to the cationic lipid and the other compounding agents in these preparations will vary as the dosage form requires.

Depending on the intended mode of administration, the pharmaceutical compositions may be in the form of solid, semi-solid or liquid dosage forms, such as, for example, tablets, suppositories, pills, capsules, powders, liquids, suspensions, lotions, creams, gels, or the like, preferably in unit dosage form suitable for single administration of a precise dosage. The compositions will include, as noted above, an effective amount of the selected lipocomplex in combination with a pharmaceutically acceptable carrier and, in addition, may include other medicinal agents, pharmaceutical agents, carriers, adjuvants, diluents, etc.

For solid compositions, conventional nontoxic solid carriers include, for example, pharmaceutical grades of mannitol, lactose, starch, magnesium stearate, sodium saccharin, talc, cellulose, glucose, sucrose, magnesium carbonate, and the like. Liquid pharmaceutically administrable compositions can, for example, be prepared by dissolving, dispersing, etc., an active compound as described herein and optional pharmaceutical adjuvants in an excipient, such as, for example, water, saline aqueous dextrose, glycerol, ethanol, and the like, to thereby form a solution or suspension. If desired, the pharmaceutical composition to be administered may also contain minor amounts of nontoxic auxiliary substances such as wetting or emulsifying agents, pH buffering agents and the like, for example, sodium acetate, sorbitan monolaurate, triethanolamine sodium acetate, triethanolamine oleate, etc. Actual methods of preparing such dosage forms are known, or will be apparent, to those skilled in this art; for example see *Remington's Pharmaceutical Sciences*, referenced above.

Parental administration, if used, is generally characterized by injection. Injectables can be prepared in conventional forms, either as liquid solutions or suspensions, solid forms suitable for solution or suspension in liquid prior to injection, or as emulsions. A more recently revised approach for parental administration involves use of a slow release or sustained release system, such that a constant level of dosage is maintained. See, e.g., U.S. Pat. No. 3,710,795, which is incorporated by reference herein.

According to the methods of the invention, both expressible DNA and mRNA can be delivered to cells to form therein a polypeptide translation product. If the nucleic acids contain the proper control sequences, they will direct the synthesis of relatively large amounts of the encoded protein. When the DNA and mRNA delivered to the cells codes for an immunizing peptide, the methods can be applied to achieve improved and more effective immunity against infectious agents, including intracellular viruses, and also against tumor cells.

Beyond the therapies described, the method of the invention can be used to deliver polynucleotides to animal stock to increase production of milk in diary cattle or muscle mass in animals that are raised for meat.

Since the immune systems of all vertebrates operate similarly, the applications described can be implemented in all vertebrate systems, comprising mammalian and avian species, as well as fish.

EXAMPLE

The compounds DOPE, DOTAP and cholesterol were purchased from Avanti Polar Lipids. Oleyl alcohol, oleyl bromide and oleyl chloride were purchased from Sigma. 3-morpholino-1,2-propanediol, 3-pyrrolino-1,2-propanediol, 2-bromoethanol, morpholine, sodium hydrate, dioxine, methanesulfonyl chloride, trimethylamine and pyridine were purchased form Aldrich. PCMV, a derivative of pCDNA3 expression vector (Invitrogen, CA), containing firefly luciferase cDNA driven by the CMV promoter, was a gift from Dr. Leaf Huang. Plasmid DNA was purified from *E coli* DH51 (Gibco BRL, MD) using standard alkaline lysis and two runs of CSC1-ethidum bromide gradient centrifugation methods described in Sambrook, J., et al., *T. Molecular Cloning*, Cold Spring Harbor Laboratory Press, New York (1989) and kept in TE (?) buffer pH 8.0. The purity of the plasmid DNA was determined by 260 and 280 nm absorbance and 0.8% agarose gel electrophoresis.

The following examples are set forth so as to provide those of ordinary skill in the art with a complete disclosure and description of how the compounds claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.) but some errors and deviations should be accounted for. Unless indicated otherwise, parts are parts by weight, temperature is in ° C. or is at room temperature, and pressure is at or near atmospheric.

Chemical Synthesis of Cationic Lipids

The synthesis of 1,2-dioleyl-3-N,N-dimethylamino propane (DODMA), 1,2-dioleyl-N-3-morpholino propane (DOMP), 1,2-dioleyl-3-pyrrolino propane (DOPP) was done in a manner similar to that previously described by Felgner (1994). Briefly, 3-dimethyl amino propanediol, 3-morpholino-1,2-propanediol or 3pyrrolino-1,2-propanediol was alkylated with oleyl methanesulfate at 140–150° C. in dioxane for 48 hours in a pressure tube to give DODMA, DOMP and DOPP respectively. After routine work-up, the crude tertiary amino lipids were purified with silica gel chromotograph using $CH_2Cl_2$/methanol. The purified tertiary amino lipids were then quaternized with methyl iodine or benzyl chloride at room temperature for 48 hours in the dark. After removing excess methyl iodine or benzyl chloride by evaporation, the residuals were dissolved in chloroform and extracted with brine. Finally quaternary ammonium lipids were purified by column chromatography with silica gel using chloroform and step increased gradient of methanol to give DOTMA, N-3-methyl-1,2-dioleyl-3-morpholinium propane chloride (methyl morpholinium ether, MMET), N-3-benzyl-1,2-dioleyl-3-morpholinium propane (BMET), -3-methyl-1,2-dioleyl-3-pyrrolinium propane (MPET), and N-3-benzyl-1,2-dioleyl-3-pyrrolinium propane (BPET).

N-3-methyl-1,2-dioleoyl-3-morpholinium propane (methyl morpholinium ester, MMES) and N-3-methyl-1,2-dioleoul-3-pyrrolinum propane (MPES) were synthesized similarly to that previously described for DOTAP by Leventis, R. et al., Biochem. Biophys. Act., 1023, 124–132. Briefly, oleyol chloride in $CH_2Cl_2$ was added to 3-morpholino-1,2-propanedio or 3-pyrrolino-1,2-propanediol in TEA/$CH_2Cl_2$ at room temperature to give 1,2-dioleoyl-3-morpholino propane and 1,2-dioleoyl-3-pyrrolino propane respectively. The tertiary amino lipids were then purified by brine extraction followed by silica gel chromatography. The quaternization and purification of the tertiary amino lipids were done similarly to the dialky lipids described above.

Preparation of Cationic Liposomes

Cationic liposomes of formulas (I–VI) were prepared from pure cationic lipids or as equimolar mixtures of a cationic lipid and neutral lipids, such as DOPE, or cholesterol, using extrusion or sonication methods. One hundred μmoles of a cationic lipid or one hundred μmoles each of a cationic lipid and a selected neutral lipid were dissolved in a round bottom flask. The organic solvent was then evaporated under vacuum at 45° C. to form a thin lipid film. The residual solvent was further removed under high vacuum for one hour. The lipid film was then suspended with 10 ml of endotoxin-free distilled water (Gibco, BRL, MD) at room temperature for one hour, and subsequently extruded using 0.8 μm, 0.4 μm and 0.2 μm pore size filters. The extruded multilammelar liposomes have sizes of 850 nm, 350 nm and 280 nm in diameter, respectively. Some of the extruded liposomes were further sonicated in a bath sonicator for 2–5 minutes to form unilamellar liposomes with a size of about 100 nm in diameter. The size of the liposomes were measured by 90° laser dynamic light scattering using a Zetamaster submicron particle analyzer.

Transfection in vivo in a Mouse Model

For transfection in vivo, normal CD-1 mouse was used as a model. The charge ration of lipid to DNA (±) was used throughout the study, assuming that 25 μg of DNA contains about 75 nmoles of negative charges, and one nmole of quaternary ammonium cationic lipid contains one nmole of positive charges. To prepare lipoplex for transfection, 25 μg or an indicated amounts of pCMV DNA was diluted in 100 μl of distilled water (endotoxin screened, Gibco). The diluted DNA solution was added to a polystyrene tube containing an indicated amount of cationic liposomes in 100 μl and was mixed immediately. The complexes were kept at + room temperature for 30 minutes before being administered to the animals via tail vein.

Luciferase Activity Assay

Luciferase activity was measured in various organs, including lung, liver spleen, and heart from transfected animals, using a luciferase activity assay kit (Promega, Madison, Wis.) and a luminometer (Moonlight 3010). Organs were collected from the animals at 12 hours post transfection or at an indicated time after injection of lipoplex. About 0.2 g of liver were removed from the animal. One ml of 1× lysis buffer (Promega, Madison, Wis.), supplemented with 0.1% Triton-X100 was added to collected organs. Each organ was homogenized for 10–20 seconds using a handheld homogenizer (Dremel, Racine, Wis.) as it top speed (about 30,000 rpm). The samples were centrifuged in a microcentrifuge for three minutes. A 10 μl of the cleared supernatant, containing approximately 100–200 μg proteins, was measured for luciferase activity. Protein content in the supernatants was determined with BioRad dye reagent method, using albumin as a standard. The luciferase activities were normalized to the relative light unit per milligram of extracted protein.

In vivo transfection activity of lipoplex is dependent on the structure of cationic lipid and the ration of lipid to DNA.

Figure 5A:
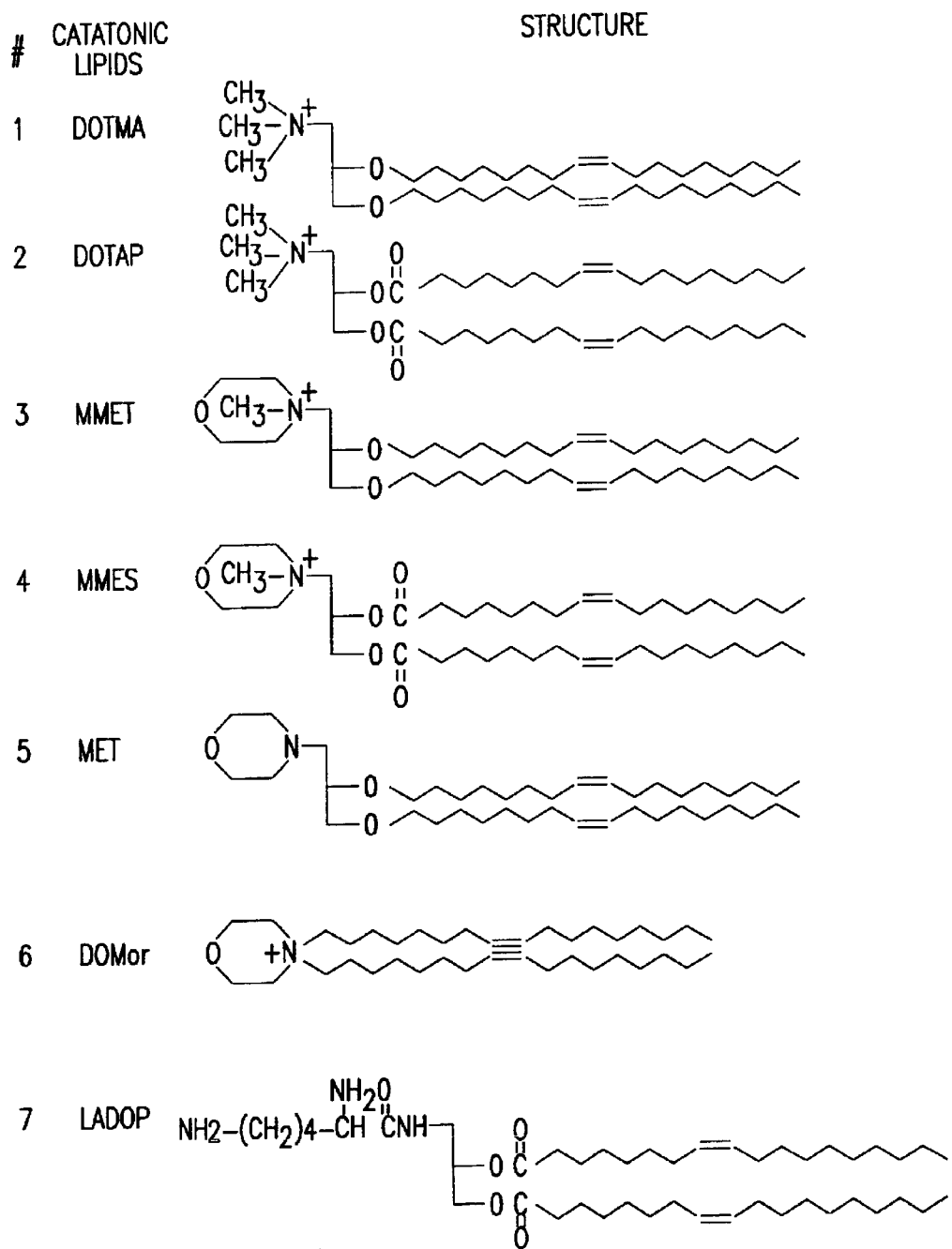
FIGS. 5A, B, and C show exemplary cationic lipids of the invention.
Figure 5B:
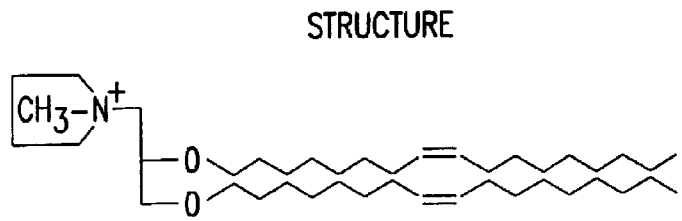
Figure 5B:
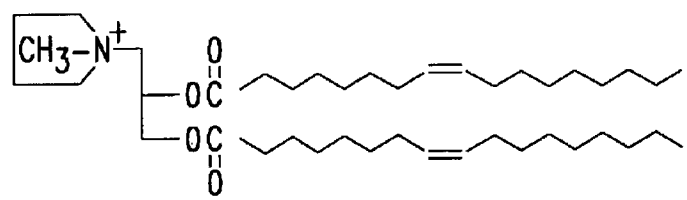
Figure 5B:
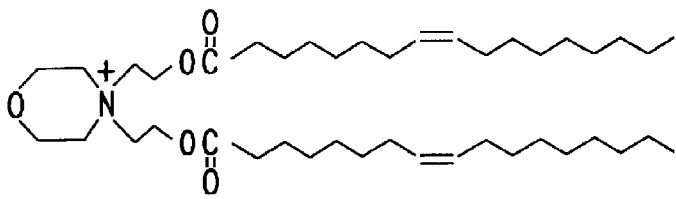
Figure 5B:
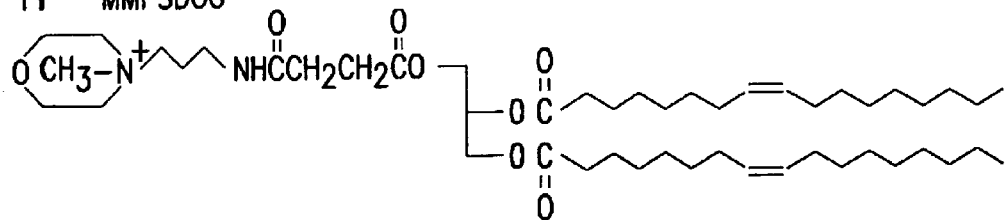
Figure 5B:
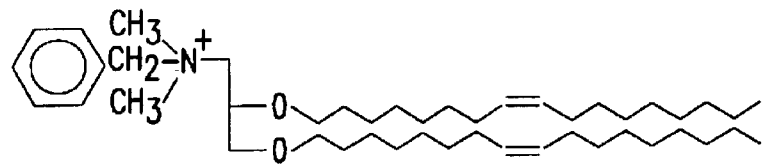
Figure 5B:
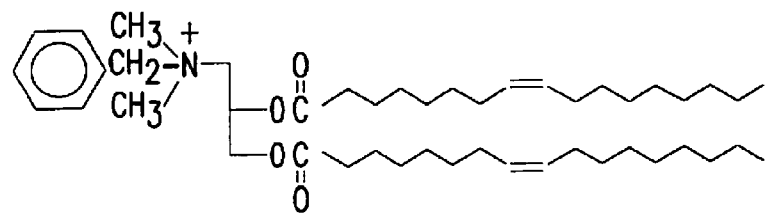
Figure 5C:
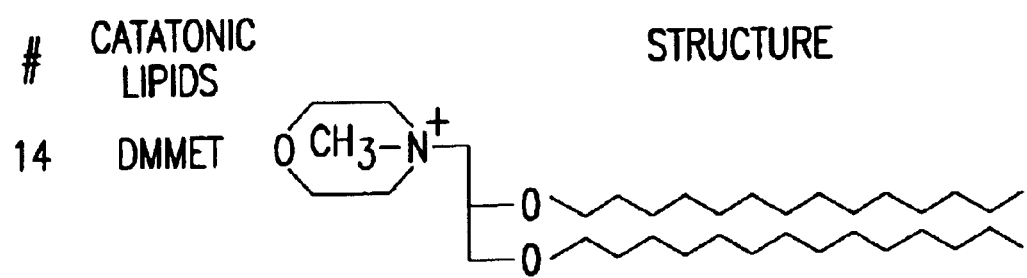

We have screened the in vivo activities of the present lipids. Among these lipids, several showed promising in vivo transfection activity. FIGS. 5A, B, and C list the chemical structures of cationic lipids that were used in this study. Among them are two well known cationic lipids, DOTAP and DOTMA, both have identical trimethylammonium head groups, glycerol interface structures and C18:1 lipid chains, but differ in the chemical bonds. DOTAP has ester bonds that link the lipid chains, whereas DOTMA has wether bonds. The new lipids belong to diester or diether bonds with different head groups: LADOP has a lysyl head group that links to a dioleyol glycerol via an amide bond, the head groups of MMES and MMET are methylated oxygen containing six-member morpholinium ring structures and the head groups of MMES and MMET are methylated oxygen containing six-member morpholinium ring structures and the head groups of MPES and MPET contains a methylated five member pyrrolinium ring structures. With the exception of the head group structures, these new lipids are close analogues to DOTAP and DOTMA, respectively. To study the significance of chemical structures related to the detailed chemical structures, the interface structures and the space arms in particular, several cationic lipids with methyl morpholinium or trimethylarnmonium head groups linked to double oleyl chains through different linker structures were also synthesized. FIG. 1 compares the in vivo transfection activity of PCMV-Luc complexed with cationic liposomes prepared from DOTAP and DOTMA in lungs 12 hours after i.v. administration with those obtained with three of our novel cationic lipids, LADOP, MMES and MMET. Different levels of luciferase activity were detected in all organs detected in all organs tested in the order of lung>heart>spleen>liver. The lungs are 10 to 1000 fold higher than the rest of the organs. For the clearance of presentation, only the specific luciferase activity in the lungs was presented in FIG. 1. It is clear that when liposomes composed of pure cationic lipids are used, the in vivo transfection activity of the lipoplex is related to the charge ratios of cationic lipid and DNA, following a trend that progressively increased luciferase activity was obtained with an increased +/− charge ratios. The highest levels of luciferase activity were observed when 16:1 +/− charge ratios were used. This is true for all five lipids tested, regardless of their chemical structures, At the ratio of 8:1 to 16:1, the transfection activity is ranked in the order of MMET≧DOTMA>MMES>DOTAP>LADOP. At 16:1 ratios, the lungs from animals treated with DNA and MMET or DOTMA liposomes resulted in luciferase activity as high as 10×7 light using units/mg protein, Further increase of charge rations failed to increase the luciferase activity. A close look also revealed that both morpholinium lipid resulted in higher levels of luciferase activity in the lungs at lower charge ratios, 4:1 +/−. So it appears that at 4:1 +/− ratios, MMET and MMES, which share a unique six-member ring quaternary ammonium structure, mediated higher levels of transfection than did their counterparts with simple trimethylammoniunm head groups, DOTMA and DOTAP, respectively, although the difference is less at higher +/− charge ratios.

Figure 2:
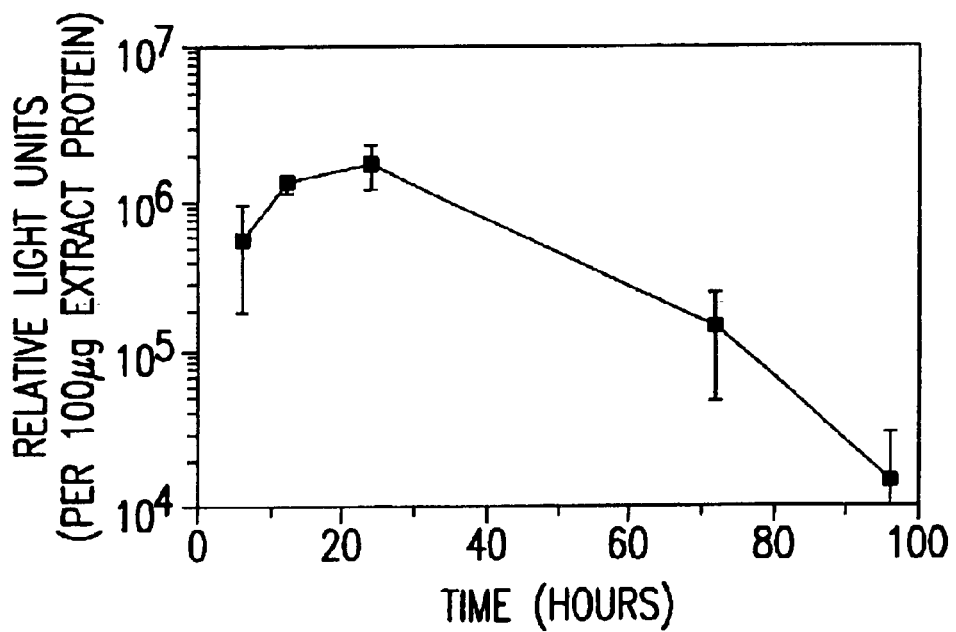
FIG. 2 shows the time course of transgene expression in mice.

Time course of luciferase gene expression in organs indicated that organs collected at 12 hours post transfection have approached the peak of gene expression, which lasted about 24 hours. The activity started to decline afterwards and reduced about 1% of peak level by 96 hours post transfection (FIG. 2).

Figure 3A:
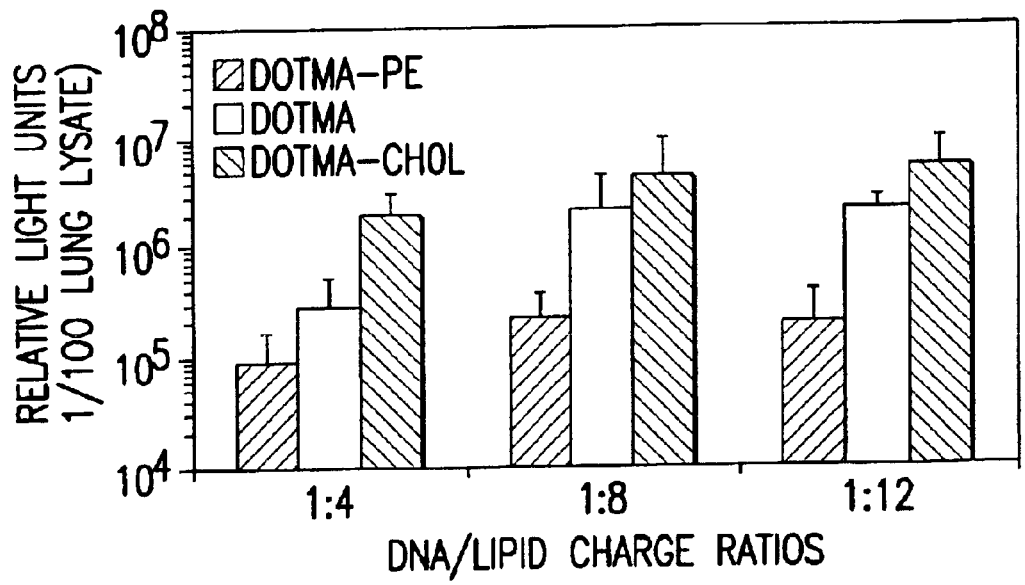
FIG. 3 shows the effect of helper lipids on cationic lipid-mediated gene transfer in vivo.
Figure 3B:
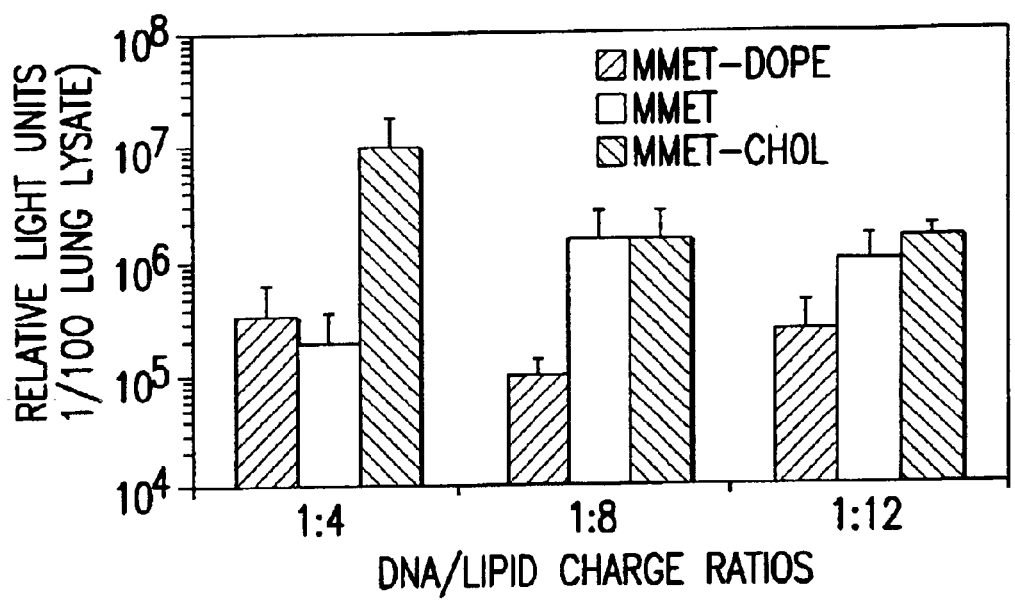

The Effects of Helper Lipid on the Level of Gene Expression and Toxicity to the Animals The effect of helper lipids on in vivo gene transfection was evaluated using DOPE and cholesterol and two cationic lipids, DOTMA and MMET. In these experiments, liposomes were prepared by extrusion method from pure cationic lipids, or 1:1 mole ratio of cationic lipid with DOPE or cholesterol. When 30 μg pCMV-Luc were used to transfect mice, at various lipid to DNA ratios (+/−), the compositions of the liposomes resulted in a drastic difference in the levels of transfection in the lung. It is evident that inclusion of DOPE in the transfection reduces the transfection activities of the cationic liposomes by a factor of 10-fold, when compared to the liposome formed with cationic lipid alone. A 1:1 mixture of cationic lipid and cholesterol, on the other hand enhances the transfection activities in lungs by 2–20 fold, depending on the nature of the cationic lipids and the charge ratio used, when compared to cationic lipids alone (FIG. 3). Despite the fact that DOTMA/cholesterol cationic liposomes are 2–10 fold more potent in transfection, in the lungs than DOTMA liposomes, the relationship between lipid/DNA charge ratios and transfection are quite similar to each other. Both showed a gradual increase in transfection activities as the +/− ratios are increased. On the other hand, MMET/cholesterol behaved very differently than MMET liposomes and liposomes containing DOTMA in that it reached the maximum transfection activity at lower charge ratios with MMET liposomes in FIG. 1, although in this experiment, the difference between DOTMA and MMET liposomes at 1:4 charge ratios is less prominent, possibly due to the increased total dose of DNA used in this experiment.

Different lipid compositions also showed different toxicity to the treated animals. Table 2 below lists the number of animals that expired during the first 48 hours of the experiment period, when escalating doses of the lipoplexes were given to a group of three animals. Lipoplex containing 25 μg of DNA and DOTMA or MMET liposomes at 1:16 charge ratio or with a mixture of cholesterol-DOTMA, or cholesterol-MMET at 1:4 charge ratios appear to be quite safe for CD-1 mice. Higher charge ratios of lipid to DNA and a high doses of lipoplex were required to reach a lethal dose. As indicated in Table 2, liposomes composed of DOTMA/DOPE or MMET/DOPE caused the least toxicity. Liposomes containing cholesterol appeared to be the most toxic, and the toxicity of DOTMA and MMET liposomes were somewhere in between. In general, MMET containing liposomes were less toxic than the ones containing DOTMA.

TABLE 2

| Treatment | Number of animals died per group (n = 3) DNA Dosage (number of animal died) | | |
|---|---|---|---|
| (16:1 +/−) | 25 ug | 30 ug | 45 ug |
| DOTMA | (0) | (2) | (3) |
| DOTMA/chol | (1) | (3) | (3) |
| DOTMA/DOPE | (0) | (0) | (1) |
| MMET | (0) | (0) | (1) |
| MMET/chol | (0) | (1) | (3) |
| MMET/DOPE | (0) | (0) | (0) |

CD-1 mice (20 g) were injected with indicated doses of DNA complexed with cationic liposomes of different compositions at a charge ratio of 1/16 (+/−). The number of survival animals was counted for each group after 48 h.

The Effect of Liposome Size on the Transfection Activity of Lipoplexes

Figure 4:
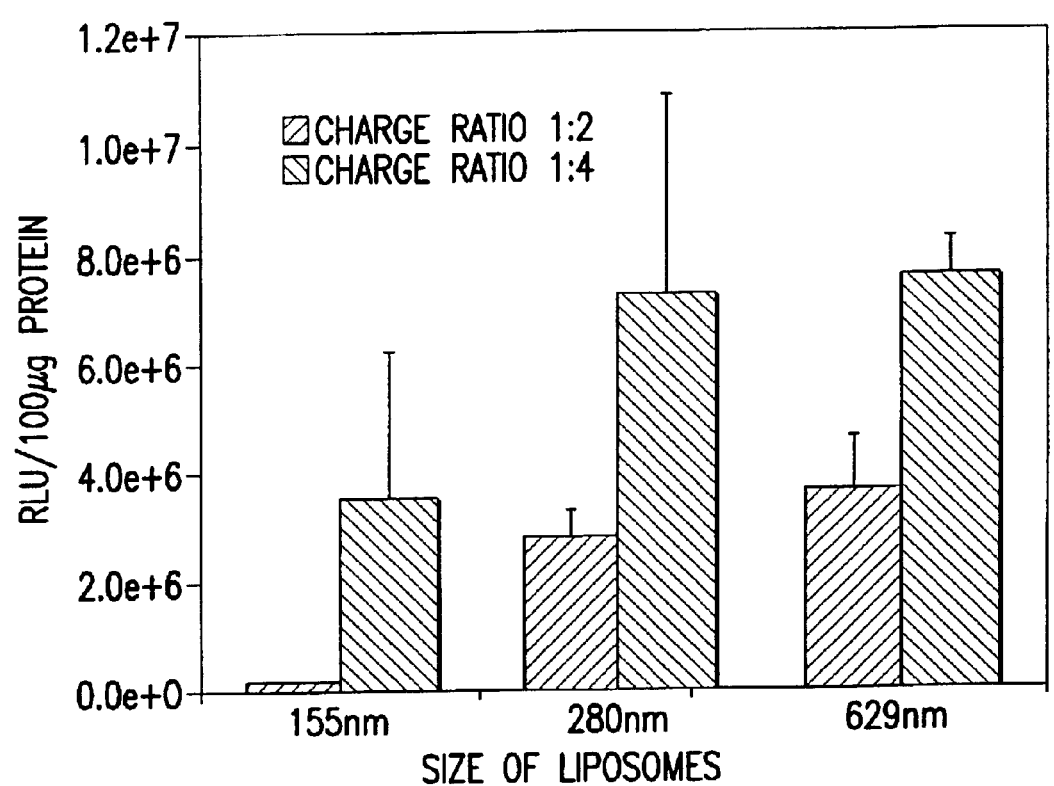
FIG. 4 shows the effect of liposome size and charge ratio on transfection of lungs.

To study the effect of the initial size of cationic liposomes on the transfection activity of cationic lipid/DNA complexes, we tested in vivo transfection activities of MMET-cholesterol liposomes of different sizes prepared by different methods. Two charge ratios were used in the this study, a 4:1+/− ratio that has been previously shown to be the most active, and a further reduced charge ratio of 2:1. In both cases, the increase of the sizes of lipoplexes was less than 50% of the sizes of the liposomes. The results are shown in FIG. 4. It is clear that at optimal ratios of 4:1 +/- or higher, liposomes with larger particle sizes prepared by the extrusion method (>=280 nm) are 2 fold more active than the small liposomes with an initial size of 155 nm prepared by the sonication method. The difference becomes more drastic when a lower charge ratio, 2:1 (+/-), is used. There is an approximate 30-fold drop in the luciferase activity in lungs transfected with small liposomes at this ratio when compared to 4:1 (+/-) ratio, whereas when using liposomes of larger sizes, lowered, 2:1 (+/-) charge ratios only resulted in a little more than 2-fold decrease. In fact, the lungs transfected with lipoplex prepared from liposomes of 280 nm in size and 2:1 (+/-) ratios achieved an excellent level of transgene expression of about 2×107 RLU/mg protein.

When we further determined the lower end of lipid to DNA ratio that was capable of transfection in vivo, we found yet another interesting phenomena, that the size of the MMET-cholesterol liposomes were also important to the in vivo transfection, particularly at a reduced +/- ratios of 2:1 (+/-) (FIG. 4). It was shown that sonicated small liposomes of 155 nm in diameter had much reduced transfection activity when used as lipid/DNA complexes at 2 to 1 (+/-) ratios. The activity was restored if higher ratios of lipid to DNA were used. However, when liposomes of 280 nm in diameter or greater were used, a significant portion of the transfection activity was obtained even at a 2:1 (+/-) ratio. With the combination of both improvements, that is by using extruded MMET-cholesterol of about 280 nm in diameter, at a ratio as low as 2:1 (+/-), we can achieve about 45% of the maximal transfection obtained using 1:4 charge ratios. Those modification allow us to transfect animals efficiently with minimal toxicity using MMET-cholesterol cationic liposomes.

Transfection Activities of the Analogues of MMET

Out of the dozen or more analogues of MMET that were synthesized and tested, most were active in transfection in vivo to the lungs when formulated with cholesterol at 1:1 mole ratios. However, none of these were superior to MMET. Table 3 below shows the transfection activities of the other novel synthesized cationic lipids listed in FIGS. 5A, B, and C. The results can be summarized as follows: (1) dioleyl morpholino propanediol, the tertiary amino lipid precursor of MMET had only weak activity; (2) N-N di-alkyl morpholinium derivatives were equally as active as the methyl morpholinium propanediol derivatives; (3) further increase in the length of spacer between head group and lipid anchor to 8 atoms reduced the transfection activity of the lipids by about 30 fold; (4) cationic lipids with methyl pyrrolinium five-member ring head groups were also active; (5) substitution of N-methyl morpholinium group with a N-benzyl group reduce the activity by 5 fold, and (6) changing the lipid chains from monounsaturated oleyl chains (C18:1) to saturated chains (C14:)) reduced the in vivo transfection activity by 10 fold. For the series of morpholinol lipids, the exact linkage between morpholinium group and lipid portion is less critical, as long as the space between the head group and the lipid anchors is not too far apart. For example, lipids with 3-N-1, 2-propandiol as backbone such as MMET, and those with N,N dialkyl lipids with or without ethylene spacer were all active.

TABLE 3

Relative Activity of MMET Analogues-Cholesterol Liposomes (1:1 mol/mol)

| | |
|---|---|
| MMET | 100 |
| DOTAP | 28.14 |
| MMES | 48.72 |
| MET | 0.87 |
| DOMor | 76.09 |
| LADOP | ND |
| MPET | 55.49 |
| MPES | 1.87 |
| DODHEM | 74.54 |
| MMPSDOG | 0.04 |
| DOBDMA | 23.85 |
| DOBDMAP | 17.95 |
| DMMET | 5.06 |

Formulation of Cationic Liposomes and Transfection Activity in vivo

Perhaps the most interesting finding in this study is the effect of cholesterol on the transfection activity and the optimal ratio of lipid to DNA to reach such a transfection level for MMET. Formulations containing cholesterol have been reported effective in vivo recently including DOTIM, DOTAP, DDAB and DOTMA cationic lipids (Solodin, I., et al., Templeton, N. S., et al., Li, S. et al., Hong, K., et al., Liu, Y. et al., and Song, Y. K., et al.). Song and his colleagues reported that DOTMA/cholesterol liposomes prepared in phosphorous buffered saline did not provide any enhanced transfection activity over liposomes prepared from DOTMA alone (Song, Y. K., et al).

It has been found in our study however, that liposomes containing equimolar cholesterol and DOTMA showed consistently 5 to 10-fold higher transfection activity over liposomes containing DOTMA alone. Similar enhancement of the transfection activity was also observed for MMET-cholesterol over MMET liposome formulation. We suspect that it is because we used water to prepare the liposome which does not cause aggregation or membrane alteration on liposome by phosphate anion. Surprisingly, MMET-cholesterol behaved quite differently from that of DOTMA-cholesterol when lower charge ratios were used to transfect mouse intravenously. MMET-cholesterol reached the maximal transfection activity at a relatively low lipid to DNA ratio of 4 to 1, whereas DOTMA-cholesterol did not reach the maximum until 16 to 1. We believe that this unique feature of MMET-cholesterol could provide high levels of transfection, while minimizing the toxicity, therefore providing greater safety for in vivo transfection.

Example 1

Synthesis of LADOP:

To a solution of 0.68 g (7.5 mmole) (+/-)-3-amino-1,2,-propanediol in 20 ml dry methanol, 1.1 ml (8 mmole) triethylamine (TEA) in 10 ml methanol was added. At room temperature, a solution of 3.1 g (7 mmole) N,N-diBoc-lysine-N-hydroxysuccinimide ester in CH2Cl2 (20 ml) was added. The reaction was allowed to continue for 1 hour, after which the solvents were evaporated. The solid was dissolved in 100 ml CHCl3 and washed with brine (200 ml) twice. The organic phase was collected and dried over sodium sulfate and the solvent was evaporated. The product was purified using 40 g silica gel to give diBoc-lysyl3-amino-1,2-propandiol 2.51 g (5.54 mmole). To a solution of 0.65 g (1.5 mmole) diBoc-lysyl3-amino-1,2-propandiol in dry CH2Cl2, 1 ml TEA and 1 ml oleic chloride (3 mmole) was added. The reaction was allowed to continue for 4 hrs. After routine work up, the product was purified with 20 g silica gel. The Boc protecting groups were then removed by trifluoroacetate(TFA)/CH2Cl2. The solvents and the excess of trifluoroacetate was removed by evaporation to yield 2.2 g final product 1,2-dioleyl-3 N-lysyl-amino-propane in trifluoroacetate salt form.

NMR spectrum data: chemical shift 0.85 (t, CH3, 6H); 1.24 (s, —CH2-50H); 1.51 (s, CH2Co2, 4H); 1.97 (s, CH2C= 8H); 2.24 (s, CH2N, 2H); 2.85 (W, CH2NCO, 2H); 3.48 (q, >CH—CO, 1H); 4.00 (w, CH2OCO, CHOCO, 3H); 5.02 (w, CO—NH, 1H); 5.30 (s, CH=CH, 4H); 7.59, 8.49, (w, —NH3+, 6H).

Example 2

Synthesis of MMET:

To a solution of 3-N-morpholino-1,2-propandiol (161 mg, 1 mmole) in 5 ml DMSO 0.4 g KOH was added. After 20 minutes, 1 g (3 mmoles) of oleyl methanesulfonate in 2 ml DMSO was added. The reaction was performed under Ar2 at room temperature for 20 h. The reaction mixture was washed with brine in hexane and purified with silica gel. The yeild of 1,2-dioleyl-3-N-morpholino-1,2-propane was 540 mg as colorless oil. To convert 1,2-dioleyl-3-N-morpholino-1,2-propane to MMET, 330 mg of 1,2-dioleyl-3-N-morpholino-1,2-propane (0.5 mmole) was dissolved in 5 ml methanol to which 500 ul of CH3I was added. The reaction was performed at room temperature at dark. The organic solvents were removed by a rotovapor. The residue were dissolved in 100 ml CHCl3 and washed with brine. The crude product was purified over silica gel to give 300 mg final product. NMR data: chemical shift: 0.84 (t, CH3, 6H); 1.23 (s, —CH2-, 44H); 1.51 (m, CH2C—O, 4H); 2.03 (m CH2C=, 8H), 3.40 (m, CH2-O—, 6H); 3.66, (14, head group H),; 5.31 (m, CH=, 4H).

Example 3

Synthesis of N-(3-dioctadecylaminopropyl)-N',N'-bis (lysyl-epsilon-lysyl)-L-lysinamide:

Synthesis of N,N-dioctadecyl-3-propyldiamine: To a suspension containing 2 g of dioctadecylamine (4 mmole), in 20 ml methanol and 20 ml CH2CL2, was added 20 ml CH2= CHCN. The reaction was contineud for 24 h at room temperature. The solvents were removed under vacuum and the product was purified with silica gel. The product was then dissolved in 20 ml ether and 2 g of LiAlH4 was added. The reduction was allowed for overnight at room temperature. The reaction was stoped with dilute NaOH in water at 0 C. The reaction mixture was filtered. The organic solvent was dried over sodium sulfate and evaporated to give 2.3 g white powder. NMR data (CDCl3): chemical shift 0.86 (t, CH3 8H); 1.24 (64H, Ch2, s), 1.49 (2H, N-C—CH2—C—N—, m); 1.59 (2H, NH2, m) 2.39 (6H, CH2N, m); 2.70 (2H, CH2N, t).

Example 4

Synthesis of N-lysyl-3-aminopropyl-N',N'-dioctadeylamine 18-1-lys:

To 0.58 g 3N-aminopropyl-NN-dioctadecylamine in 20 ml CH2CL2 was added with 0.49 g (1.1 mmole) di-Boc-lysine NHS ester in 20 ml CH2Cl2. After 2 h the reaction was stopped and extracted with dilute NaOH in water, dried over sodium sulfate. The product was purified on silica gel and deprotected with TFA/CH2Cl2 as in LADOP synthesis to give 0.5 g desired product.

NMR data: (CDCl3) 0.86 (6H, CH3, t); 1.24 (64H, CH2, s); 1.66 (8H, CH2), 2.01 (4H, NH2); 3.03 (10H, CH2N); 4.19 (1H, alpha Hon lysine group), 7.99 (1H, HNCO).

Example 5

Synthesis of intermediate 18-1-(Lys)3-CBZ2:

To 1.41 g of the immediate 18-1-lys (2 mmole) in 20 ml CH2Cl2, 0.56 ml TEA (4 mmole) and 2.01 g CBZ(Boc)-lysine NHS ester in 20 ml CH2Cl2 was added. The reaction was carried out at room temperature for 2 h. After routine work up, the product was purified with silica gel to give 1.7 g white solid. The Boc groups were removed with TFA/CH2Cl2 and washed with dilute NaOH to give 1.3 g 18-1-lys3-CBZ2 (1 mmole).

Example 6

Synthesis of 18-1-(lys)5:

1.3 g of the intermediate 18-1-lys3-CBZ2 (1 mmole) and 0.42 ml TEA in 50 ml CH2Cl2 was added 4.2 g of CBZ (Boc)-lysine NHS ester in 50 ml CH2CL2. After 2 h, the reaction was stopped and worked up. The product was purified with silica gel. Purified product (0.83 g) was treated with TFA/CH2Cl2 to remove Boc groups to give 0.8 g 18-1-lys5-CBZ4. From 520 mg of 18-1-lys5-CBZ4, the CBZ groups were removed by Pd/H2 in 10 ml ethanol with 0.5 ml acetic acid at room temperature under 1 atm for 2 h to give final product (0.44 g).

Example 7

Synthesis of Heterocyclic compound:

N-benzyl-NN-dimethyl-[2,3-dioleoyloxypropyl) ammonium chloride

To 300 mg of 3-N,N-dimethylamino-1,2-propandiol (3 mmole) and 500 ul of TEA in 10 ml dioxane, 2.1 g of oleyol chloride in 10 ml CH2Cl2 (7 mmole) was added. The reaction was carried out at room temperature for 2 h. After routine work up, the product was purified with silica gel, yeilding 2.2 g of 1,2-dioleoyl -3-N,N-dimethylamionpropane (DODAP). To a solution of 619 mg (1 mmole) of DODAP in 20 ml ethanol, 1.26 g (10 mmole) benzyl chloride was added and refluxed for 72 h under Ar2. The reaction was stopped and organic solvents evaporated. The product was purified on silica gel to give 120 mg of desired compound in chloride form.

Example 8

Synthesis of Cholestoryl derivatives (2 examples):

N,N-dimethyl-N-[2-(cholesteryl-carboxylmethylthioethyl]amine

To a solution of 1.4 g 2-dimethylaminoethyanethiol hrydrochloride (10 mmole) in ethanol, 463 mg of cholesteryl chloroacetate in 20 ml CH2Cl2 and 1 ml TEA were added. The reaction was carried out at room temperature for 2 days. The resulting mixture was worked up as routine and the product was purified by silica gel, yeilding 210 mg of desired compound.

N-cholestylidenediazanyl)-carbonylmethylN,N,N-trimethyl ammonium chloride.

To a solution of 390 mg of 5-alpha-cholestan-3-one in 10 ml ethanol and 170 mg (1 mmole) carbonylmethylN,N,N-trimethyl ammonium chloride hydrazide in 10 ml methanol was added. The soltuions was heated slightly and 2 g of molecular sieves (4A) and 5 ul of HCl (conc.) was added. The reaction was carried out for overnight at room tempera-

Example 9

Synthesis of 1,2-O-dioleoyl-3-[(2-dimethylaminoethyl)thioacetyl]-sn-glycerol:

(Step 1) To 1.75 g of dioleyl-sn-glycerol in 13 ml CHCL3 and 0.78 ml TEA, 1.16 g Bromoacetylbromide in 10 ml CHCl3 was added. The reaction was carried out at 4 C overnight. The reaction was stopped by dilution with 100 ml CH2Cl2 and washed twice with 100 ml diluted citric acid (0.1 M) twice and once with water. The organic phase was dried over sodium sulfate then purified with silica gel to give 1.88 g 1,2-di-oleoyl-3-beta-bromoacetyl-sn-glycerol as oil.

(Step 2) To 0.37 g (0.5 mmole) 1,2-di-oleoyl-3-(2-bromoacetyl)-sn-glycerol in 5 ml CHCl3 was added 0.07 g (0.5 mmole) 2-dimethylaminoethanethiol hydrochloried and 0.1 g (1 mmole) sodium carbonate in 5 ml methanol. The reaction was carried out at room temperature overnight. After routine work up, the final product was purified using silica gel to give 0.2 g colorless oil.

Example 10

Synthesis of S-methyl-S-(2-trimethylaminoethyl)-S-[(2,3-dioleoylpropoxy) carbonylmethane]sulfonium diiodide:

To a solution of 100 mg of 1,2-O-dioleoyl-3-[(2-dimethylaminoethyl)thioacetyl]-sn-glycerol in 5 ml methanol, 100 ul of CH3I was added. The reaction was carried out at room temperature overnight at dark. After romoval of solvants, the product was obtained by silica gel purification.

Example 11

Synthesis of N',N'-dioctadecyl-4-(3'-aminopropyl)-4-azahexane-1,7-diamine:

To a solution of 1 g N,N-dioctadecyl-3-propyldiamine in 40 ml methanol, 10 ml acrylnitrile was added. The reaction was carried out at room temperature for three days. The organic solvents was evaporated. The reaction mixture was purified on silica gel. About 0.7 g of di-substituted amine was obtained, remaining was mono-substitute. The di-substitute intermediate was dissolved in 10 ml ether and 0.1 g of LiAlH4 was added at 0 C. The reation was stopped after 2 h with diluted NaOH and extracted with 100 ml hexane and filtrated. The filtrate was washed twice with water and dried by sodium sulfate. After evaporation of organic solvents, a yellowish oil was obtained which give a major spot on TLC that was reactive with flourescamine indicated primary amine. To facilitate the purification, the crude amine was reacted with excess of Boc anhydrate and TEA in CHCl3 to give di-Boc-diamine as major spot on TLC. The boc-substituted diamine was purified from silica gel. Finally this intermediate was deprotected with TFA/CH2Cl2 and washed with diluted Na2CO3 and dried to give desired product.

Example 12

Synthesis of 8-(3-N,N-dioctadecylaminopropyl)-4,8,12-triazapemntadecane-1,15-diamine (12a) and 4,12-di(3-aminopropyl)-8-(3-N,N-dioctadecylaminopropyl)-4,8,12-triazapentadecane-1,15-diamine (12b)

To a solution of 3 g of N',N'-dioctadecyl-4-(3'-aminopropyl)-4-azahexane-1,7-diamine (Ex. 11) in methanol: CHCl3 1:1, 20 ml acylnitrile was added. The reaction was carried at 60 C for 40 minute then room temperature for 3 days. The mixture was purifed on silica gel to give di-substituted and tetra-substituted intermediates of N',N'-dioctadecyl-4-(3'-aminopropyl)-4-azahexane-1,7-diamine (Ex. 11). Follow the same reduction condition described above for the synthesis of N',N'-dioctadecyl-4-(3'-aminopropyl)-4-azahexane-1,7-diamine (Ex. 11), 8-(3-N,N-dioctadecylaminopropyl)-4,8,12-triazapemntadecane-1,15-diamine (12a) was prepared from di-substituted N',N'-dioctadecyl-4-(3'-aminopropyl)-4-azahexane-1,7-diamine (Ex. 11), and 4,12-di(3-aminopropyl)-8-(3-N,N-dioctadecylaminopropyl)-4,8,12-triazapentadecane-1,15-diamine (12b) from tetra-substituted N',N'-dioctadecyl-4-(3'-aminopropyl)-4-azahexane-1,7-diamine (Ex. 11).

Example 13

Synthesis of N,N-bis(3-1-lysylaminopropyl)-N',N'-dioctadecylpropyldiamine:

To a solution of 0.9 g (1.3 mmole) N',N'-dioctadecyl-4-(3'-aminopropyl)-4-azahexane-1,7-diamine (Ex. 11) in 40 ml CH2Cl2, 1.2 g (2.7 mmoles) of di-Boc-Lysine ester in 40 ml and 2 ml of TEA was added. The reaction was stopped at 2 h, washed with diluted Na2CO3 and water and dried over Na2SO4. The Bis Boc-lysyl derivative of N',N'-dioctadecyl-4-(3'-aminopropyl)-4-azahexane-1,7-diamine was purified from the crude product by silica gel. The desired product, N,N-bis(3-1-lysylaminopropyl)-N',N'-dioctadecylpropyldiamine was obtained as HCl salt after treatment at room temperature for 1 h with 20 ml 1M-HCl in ether followed by removal of excess of HCl and solvents.

Example 14

Synthesis of N-(3-dioctadencylaminopropyl)-alpha, epsilon-bis-L-lysyl-L-lysylamide (18-1-lys3):

To a solution of 706 mg (1 mmole) of N-lysyl-3-aminopropyl-N',N'-dioctadeylamine in 50 ml CHCl3 and 0.28 ml (2 mmole) of TEA976 mg (2.2 mmoles) of di-Boc-lysine-NHS ester in 50 ml CHCl3 was added. The reaction was carried out at room temperature overnight. After routine work up, the crude product was purified with siliga gel to give 0.65 g white solid of pure bis-Boclysyl derivative of N-lysyl-3-aminopropyl-N',N'-dioctadeylamine. The desired compound was obtained by deprotection of the bis-Boclysyl derivative with 10 ml CH2Cl2/10 ml TFA to give 0.45 g N-(3-dioctadencylaminopropyl)-alpha, epsilon-bis-lysyl-lysylamide in TFA salt as white solid.

Example 15

Synthesis of N-(3-dioctadencylaminopropyl)-alpha, epsilon-hepta-L-lysyl-L-lysylamide (18-1-lys7d):

To a solution of 0.75 g (0.78 mmole) of N-(3-dioctadencylaminopropyl)-alpha, epsilon-bis-L-lysyl-L-lysylamide (18-1-lys3) in 50 ml CHCl3 and 0.56 ml TEA (4 mmoles), 2 g (4.4 mmoles) of diBoc-lysine NHS ester in 50 ml CHCl3 was added. After 2 h, the reaction was stopped by washing with Brine, water. The crude product was subjected to silica gel column purification to give 1.21 g white solid of tetra-substitute of N-(3-dioctadencylaminopropyl)-alpha, epsilon-bis-L-lysyl-L-lysylamide. The Boc groups was removed by the treatment of 100 ml 1 M HC in ether for 30 minutes. Evaporation of organic solvents under vacuum gave 0.82 g of white solid of N-(3-dioctadencylaminopropyl)-alpha, epsilon-hepta-L-lysyl-L-lysylamide in the form of HCl salt.

Example 16

Synthesis of N-(3-dioctadencylaminopropyl)-alpha-L-lysyl-L-lysylamide; N-(3-dioctadencylaminopropyl)-alpha-L-di-lysyl-L-lysylamide; N-(3-dioctadencylaminopropyl)-alpha-L-tri-lysyl-L-lysylamide; N-(3-dioctadencylaminopropyl)-alpha-L-tetra-lysyl-L-lysylamide; N-(3-dioctadencylaminopropyl)-alpha-L-penta-lysyl-L-lysylamide; N-(3-dioctadencylaminopropyl)-alpha-L-hexa-lysyl-L-lysylamide.

To a solution of 2.31 g (4 mmoles) of N,N-dioctadecyl-1,3-propyldiamine (18-1) in 50 ml of CHCl3 and 0.8 ml of TEA (5.7 mmoles), 2.51 g (4.2 mmoles) of alpha-Boc-epislon-CBZ-L-lysine NHS ester in 50 ml CHCl3 was added. After 1 h, the reaction was stopped. After routine work up, the product was purified with silica gel column separation to give 3.7 g white solid, which was then treated with 10 ml TFA/CH2Cl2 for 30 minutes at room temperature to give 3.3 yellowish oil after evaporation of solvents and TFA. The intermediate was dissolved in 50 ml CHCl3 to which 4 ml TEA and 2.51 g (4.2 mmole) of alpha-Boc-epislon-CBZ-L-lysine NHS ester in 50 ml CHCl3 was added. The reaction was carried out overnight. The product was treated and purified essentially as above to give 3.78 g of alpha-Boc-epislon-CBZ-alpha-L-lysyl-epislon-CBZ-lysylamide of N,N-dioctadecyl-3-propylamine. This cycle was repeated to generate oligolysylamide of N,N-dioctadecyl-3-propylamine with n=2-7 in lysyl numbers whose epislon NH2 groups were protected by CBZ groups. The final step involved the removal of CBZ groups from epislon NH2 groups of lysyl residue by H2/Pt treatment in ethanol solution for 2 h at 1 atm. to give N-3(-N',N'-dioctadecylaminopropyl)-alpha-L-di, tri, tetra, penta, and hexa-L-lysinamide, respectively.

Example 17

Synthesis of N,N-dioleylmorpholinium chloride:

To 1.66 g of oleyl bromide (5 mmole), 174 mg (2 mmoles) of morpholine was added. The mixture was stirred for 4 h at room temperature. After that 318 mg of Na2CO3 (3 mmoles) and 10 ml ethanol was added and the mixture was refluxed for four days. The desired compound, dioleylmorpholinium chloride was obtained after silica gel column purification in an yield of 131 mg.

Example 18

Synthesis of N,N-di-(2-oleyloxyethyl)-mopholinium chloride:

To 213 ul (3 mmoles) of 2-bromoethanol, 363 ul (3 mmoles) of N-(2-hydroxyl)-morpholin was added to 10 ml dioxane in a presure tube. The reaction was initiated for 3 days at 130 C. After that the organic solvents and excess of reactant was removed by high vacuum. To prepare desired compound, theintermediate (950 mg, 3.7 mmoles) was dissolved in 20 ml CHCl3, to which 2.64 ml TEA and 2.4 g (8 mmoles) of oleoyl chloride in 20 ml CHCl3 was added. After reaction overnight at room temperature, the reaction was stopped. The reaction mixture was washed with brine. The crude product was purified with silica gel column to yield 226 mg of desired compound.

Example 19

Synthesis of poly[2-(dimethylaminotetramethylene aminocarbonyl)-1,5-pentanediamine 1,16 hexadecadiamide:

To a solution of N,N-dimethylpropanediamine in CHCl$_3$, 1.1 mol equivalent of diBoclysine NHS ester and 1 mol equivalent of TEA was added. The reaction was allowed for 2 h at room temperature. After routine work up, the intermediate was purified by silica gel column. The N-di-Boc-lysyl-N'N'-dimethylpropanediamine were treated with CH2Cl2/TFA to remove Boc-groups to yield lysyl-N'N'-dimethylpropanediamine. To prepare the desired polymer, to a solution of the above lysyl derivative in dimethylforamide and 2 mol equ. of TEA was added followed by equal volume of a solution of equ mol of 1–16 hexadecaneic dichloride was added dropwise with stirring. The reaction was carried out in room temperature for overnight. After removal of solvent, the product was purified by repeat acid dissolution/base precipitation followed by centrifugation. Finally, the polymer was dried under high vacuum.

Throughout this application, various publications are referenced. The disclosures of these publications in their entireties are hereby incorporated by reference into this application in order to more fully describe the state of the art to which this invention pertains.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A liposome formulation comprising a compound selected from the group consisting of:

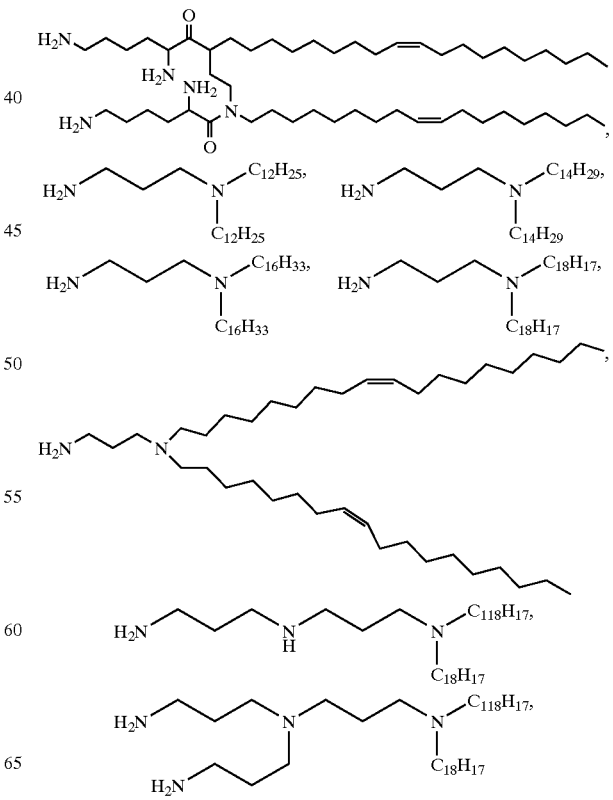

-continued
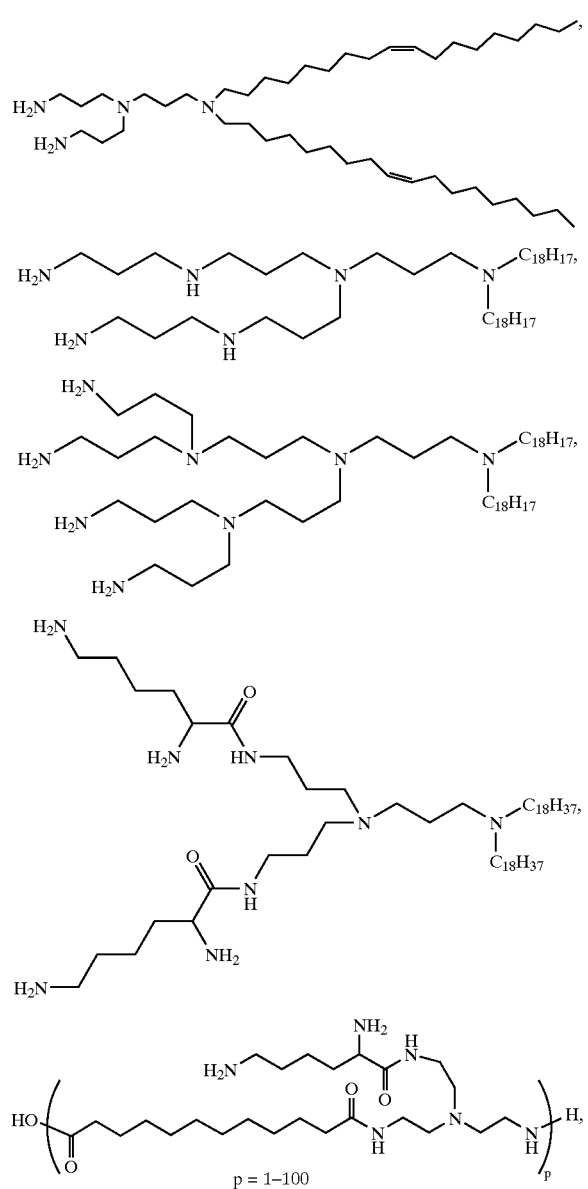
-continued
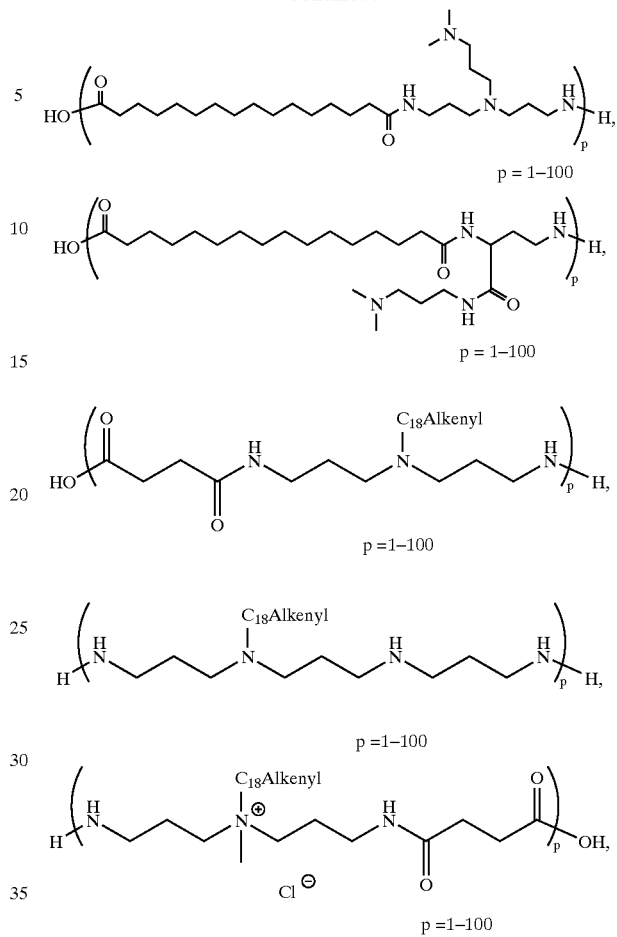
or a pharmaceutically acceptable salt or ester thereof, wherein the liposome formulation is suitable to deliver bioactive substances intracellularly either in vitro or in vivo.
* * * * *